United States Patent
Valdastri et al.

(10) Patent No.: US 9,826,904 B2
(45) Date of Patent: Nov. 28, 2017

(54) SYSTEM AND METHOD FOR DETECTING TISSUE SURFACE PROPERTIES

(71) Applicant: Vanderbilt University, Nashville, TN (US)

(72) Inventors: Pietro Valdastri, Nashville, TN (US); Marco Beccani, Nashville, TN (US); Christian Di Natali, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 706 days.

(21) Appl. No.: 14/220,991

(22) Filed: Mar. 20, 2014

(65) Prior Publication Data
US 2014/0206953 A1 Jul. 24, 2014

Related U.S. Application Data

(63) Continuation-in-part of application No. 14/027,561, filed on Sep. 16, 2013, now abandoned.
(Continued)

(51) Int. Cl.
*A61B 5/00* (2006.01)
*A61B 5/05* (2006.01)
(Continued)

(52) U.S. Cl.
CPC .......... *A61B 5/0053* (2013.01); *A61B 5/0031* (2013.01); *A61B 5/05* (2013.01);
(Continued)

(58) Field of Classification Search
CPC .......... A61B 2017/00221; A61B 2017/00283; A61B 2017/00876; A61B 2090/064; A61B 2562/0223
See application file for complete search history.

(56) References Cited

U.S. PATENT DOCUMENTS

| | | |
|---|---|---|
| 3,315,660 A | 4/1967 | Abella |
| 3,858,572 A | 1/1975 | Binard et al. |

(Continued)

FOREIGN PATENT DOCUMENTS

| | | |
|---|---|---|
| DE | 102006019419 | 11/2007 |
| EP | 2163206 | 3/2010 |

(Continued)

OTHER PUBLICATIONS

PCT International Search Report and Written Opinion for Application No. PCT/US2015/049142 dated Dec. 11, 2015.
(Continued)

*Primary Examiner* — Baisakhi Roy
(74) *Attorney, Agent, or Firm* — Michael Best & Friedrich LLP

(57) ABSTRACT

A system and method for detecting a tissue property. The system comprises a first unit positioned outside a patient body and a second unit positioned inside the patient's body. The first unit includes a first housing, and a magnetic field source supported by the first housing. The second unit includes a second housing, a pressure sensor supported by the second housing, a localization module supported by the second housing, a controller, and a power source. The pressure sensor is configured to detect an indentation force applied to the tissue, and the second unit is configured to wirelessly transmit the indentation force data and localization data to a computer to generate a volumetric stiffness map for the tissue.

20 Claims, 21 Drawing Sheets

Related U.S. Application Data

(60) Provisional application No. 61/803,700, filed on Mar. 20, 2013, provisional application No. 61/701,447, filed on Sep. 14, 2012.

(51) Int. Cl.
*A61B 5/11* (2006.01)
*A61B 34/00* (2016.01)
A61B 17/00 (2006.01)
A61B 90/00 (2016.01)

(52) U.S. Cl.
CPC .............. *A61B 5/11* (2013.01); *A61B 5/4887* (2013.01); *A61B 5/6861* (2013.01); *A61B 5/6885* (2013.01); *A61B 34/76* (2016.02); A61B 2017/00221 (2013.01); A61B 2017/00283 (2013.01); A61B 2017/00876 (2013.01); A61B 2090/064 (2016.02); A61B 2562/0223 (2013.01); A61B 2562/0252 (2013.01)

(56) References Cited

U.S. PATENT DOCUMENTS

| | | | |
|---|---|---|---|
| 3,870,072 A | 3/1975 | Lindemann | |
| 4,048,992 A | 9/1977 | Lindemann et al. | |
| 4,207,887 A | 6/1980 | Hiltebrandt et al. | |
| 5,489,256 A | 2/1996 | Adair | |
| 6,248,080 B1* | 6/2001 | Miesel | A61B 5/0215 600/311 |
| 6,270,787 B1 | 8/2001 | Ayer | |
| 6,802,811 B1* | 10/2004 | Slepian | A61B 5/0031 600/309 |
| 7,722,559 B2 | 5/2010 | Uesugi et al. | |
| 2001/0051766 A1 | 12/2001 | Gazdzinski | |
| 2003/0114731 A1 | 6/2003 | Cadeddu et al. | |
| 2005/0277852 A1* | 12/2005 | Shih | A61B 5/0053 600/587 |
| 2008/0015413 A1 | 1/2008 | Barlow et al. | |
| 2008/0021334 A1 | 1/2008 | Finburgh et al. | |
| 2008/0058835 A1 | 3/2008 | Farritor et al. | |
| 2008/0154093 A1 | 6/2008 | Cho et al. | |
| 2008/0207999 A1 | 8/2008 | Abraham-Fuchs et al. | |
| 2009/0054877 A1 | 2/2009 | Hood et al. | |
| 2009/0171268 A1 | 7/2009 | Williams, Jr. et al. | |
| 2009/0171373 A1 | 7/2009 | Farritor et al. | |
| 2009/0292205 A1* | 11/2009 | Osaka | A61B 8/08 600/443 |
| 2010/0100117 A1 | 4/2010 | Brister et al. | |
| 2010/0198008 A1 | 8/2010 | Kawano | |
| 2010/0256636 A1 | 10/2010 | Fernandez et al. | |
| 2011/0184235 A1 | 7/2011 | Schostek et al. | |
| 2011/0202070 A1 | 8/2011 | Dario et al. | |
| 2011/0301497 A1* | 12/2011 | Shachar | A61B 1/00158 600/567 |
| 2011/0313415 A1 | 12/2011 | Fernandez et al. | |
| 2012/0035416 A1 | 2/2012 | Fernandez et al. | |
| 2012/0041345 A1 | 2/2012 | Rajamani et al. | |
| 2012/0149981 A1 | 6/2012 | Khait et al. | |
| 2012/0238796 A1* | 9/2012 | Conlon | A61B 1/00158 600/9 |
| 2012/0271555 A1* | 10/2012 | Levental | A61B 5/0057 702/19 |
| 2013/0131695 A1 | 5/2013 | Scarfogliero et al. | |
| 2013/0165859 A1 | 6/2013 | Imran | |
| 2013/0225922 A1 | 8/2013 | Schentag et al. | |
| 2013/0245356 A1* | 9/2013 | Fernandez | A61B 34/70 600/12 |
| 2013/0298715 A1 | 11/2013 | Valdastri et al. | |
| 2013/0324914 A1 | 12/2013 | Valdastri et al. | |

FOREIGN PATENT DOCUMENTS

| | | |
|---|---|---|
| EP | 2286756 | 2/2011 |
| WO | 0030548 | 6/2000 |
| WO | 2004041068 | 5/2004 |
| WO | 2007013059 | 2/2007 |
| WO | 2007146987 | 12/2007 |
| WO | 2008122997 | 10/2008 |
| WO | 2009014917 | 1/2009 |
| WO | 2010042611 | 4/2010 |
| WO | 2010044053 | 4/2010 |
| WO | 2010046823 | 4/2010 |
| WO | 2011058505 | 5/2011 |
| WO | 2011135503 | 11/2011 |
| WO | 2012028557 | 3/2012 |
| WO | 2012035157 | 3/2012 |
| WO | 2012080947 | 6/2012 |
| WO | 2012164517 | 12/2012 |
| WO | 2013027182 | 2/2013 |

OTHER PUBLICATIONS

F. Carpi, N. Kastelein, M.Talcott, and C.Pappone. Magnetically controllable gastrointestinal steering ofvideo capsules. IEEE Transactions on Biomedical Engineering, 58:231-234, 2011.

J. Keller, C. Fibbe, F. Volke, J. Gerber, A. C. Mosse, M. Reimann-Zawadzki, E. Rabinovitz, P. Layer,D. S. and V. Andresen, U. Rosien, and P. Swain. Inspection of the human stomach using remote controlled capsule endoscopy: a feasibility study in healthy volunteers. Gastrointestinal Endoscopy,73:22-28, 2011.

S. Park, R. Bergs, R. Eberhart, L. Baker, R. Fernandez, and J. Cadeddu. Trocar-less instrumentation forlaparoscopy: magnetic positioning of intra-abdominal camera and retractor. Annals of Surgery,245:379-384, 2007.

J. F. Rey, H. Ogata, N. Hosoe, K. Ohtsuka, N. Ogata, K. Ikeda, H. Aihara, I. Pangtay, T. Hibi, S. Kudo,and H. Tajiri. Feasibility of stomach exploration with a guided capsule endoscope. Endoscopy, 42:541-545, 2010.

P. Swain, R. Austin, K. Bally, and R. Trusty. Development and testing of a tethered, independentcamera for NOTES and single-site laparoscopic procedures. Surgical Endoscopy, 24:2013-2021, 2010.

P. Valdastri, G. Ciuti, A. Verbeni, A. Menciassi, P. Dario, A. Arezzo, M. Morino. Magnetic air capsulerobotic system: Proof of concept of a novel approach for painless colonoscopy. Surgical Endoscopy,2011, in press.

G. Ostrovsky, Preview of Magnetically Guided Colonoscopy from Vanderbilt. MedGadget press release:http://medgadget.com/2011/10/preview-of-magnetically-guided-colonoscopy-from-vanderbilt.html.

A. Fritscher-Ravens, S. Fox, C.P. Swain, P. Mills, and G. Long. Cathcam guide wire-directedcolonoscopy: first pilot study in patients with a previous incomplete colonoscopy. Endoscopy, 38:209-213, 2006.

B. Vucelic, D. Rex, R. Pulanic, J. Pfefer, I. Hrstic, B. Levin, Z. Halpern, and N. Arber. The Aer-o-Scope: proof of concept of a pneumatic, skill-independent, self-propelling, self-navigating colonoscope.Gastroenterology, 130:672-677, 2006.

F. Cosentino, E. Tumino, G.R. Passoni, E. Morandi, and A. Capria. Functional evaluation of theEndotics System, a new disposable self-propelled robotic colonoscope: in vitro tests and clinical trial. International Journal of Artificial Organs, 32:517-527, 2009.

M. Shike, Z. Fireman, R. Eliakim, O. Segol, A. Sloyer, L.B. Cohen, S. Goldfarb-Albak, and A. Repici.Sightline Colonosight system for a disposable, power-assisted, non-fiber-optic colonoscopy.Gastrointestinal Endoscopy, 68:701-710, 2008.

T. Rösch, A. Adler, H. Pohl, E. Wettschureck, M. Koch, B. Wiedenmann, and N. Hoepner. A motor-driven single-use colonoscope controlled with a hand-held device: a feasibility study involunteers. Gastrointestinal Endoscopy, 67:1139-1146, 2008.

A. Eickhoff, J. Van Dam, R. Jakobs, V. Kudis, D. Hartmann, U. Damian, U. Weickert, D. Schilling, andJ.F. Riemann. Computer-assisted colonoscopy (the NeoGuide endoscopy system): results of

(56) References Cited

OTHER PUBLICATIONS the firsthuman clinical trial (pace study). The American Journal of Gastroenterology, 102:261-266, 2007.

M. Moshkowitz, Y. Hirsch, I. Carmel, T. Duvdevany, I. Fabian, E.P. Willenz, and J. Cohen. A noveldevice for rapid cleaning of poorly prepared colons. Endoscopy, 42:834-836, 2010.

A. Fritscher-Ravens, C. Mosse, T. Mills, K. Ikeda, P. Swain, Colon cleaning during colonoscopy: a newmechanical cleaning device tested in a porcine model. Gastrointestinal Endoscopy, 63:141-143, 2006.

H. Richert, B. Hilgenfeld, and P. Gomert, "Magnetic sensor techniques for new intelligent endoscopic capsules," http://www.vector-project.com/press/artike/VECTOR%20article_Richert_MagneticSensorTechniques.pdf, publicly available prior to Sep. 17, 2012.

Than, T. D.; Alici, G.; Zhou, H.; Li, W.;, "A Review of Localization Systems for Robotic Endoscopic Capsules," Biomedical Engineering, IEEE Transactions on , vol. 59, No. 9, pp. 2387-2399, Sep. 2012.

NDI Medical's Aurora product, http://www.ndigital.com/medical/products/aurora/, publicly available prior to Sep. 17, 2012.

M. B. H. Gerald Rogers. The safety of carbon dioxide insufflation during colonoscopic electro-surgical polypectomy. Gastrointestinal Endoscopy, 20:115-117, 1974.

Bracco. Co2 efficient endoscopic insufflator.

P. E. J.-M. D. Filip Janssens, Jacques Deviere. Carbon dioxide for gut distension during digestive endoscopy: Technique and practice survey. World Journal of Gastroenterology, 15(12):1475-1479, 2009.

F. A. Macrae, K. G. Tan, and C. B. Williams. Towards safer colonoscopy: a report on thecomplications of 5000 diagnostic or therapeutic colonoscopies. Gut, 24(5):376{383, 1983.

W. J. R. P. Phaosawasdi K, Cooley W. Carbon dioxide-insufflated colonoscopy: an ignoredsuperior technique. Gastrointestinal Endoscopy, 32:330-333, 1986.

K. Sumanac, I. Zealley, B. M. Fox, J. Rawlinson, B. Salena, J. K. Marshall, G. W. Stevenson,and R. H. Hunt. Minimizing postcolonoscopy abdominal pain by using fCO2g insufflation: Aprospective, randomized, double blind, controlled trial evaluating a new commercially availablefCO2g delivery system. Gastrointestinal Endoscopy, 56(2):190-194, 2002.

J. C. H. Wong, K. K. Yau, H. Y. S. Cheung, D. C. T. Wong, C. C. Chung, and M. K. W. Li.Towards painless colonoscopy: A randomized controlled trial on carbon dioxide-insufflatingcolonoscopy. ANZ Journal of Surgery, 78(10):871-874, 2008.

PCT International Search Report and Written Opinion for Application No. PCT/EP2011/064764 dated Oct. 10, 2011.

Toennies, J.L. et al., "A Wireless Insufflation System for Capsular Endoscopes," Journal of Medical Devices, vol. 3 (Jun. 2009).

Toennies, Jenna L. et al., "Initial Feasibility Studies on Wireless Insufflation of the GI Tract," IEEE International Conference on Robotics and Automation 2010—Workshop on Meso-ScaleRobotics for Medical Interventions, (May 3, 2010).

Smith, Byron, "Wireless Insufflation for Wireless Capsule Endoscopy," Vanderbilt University Master's Thesis (Aug. 2012).

Pedersen, Amanda, "Capsule Endoscopy in ER Could Drop Admission Rate," Medical Device Daily (Feb. 13, 2013).

PillCam Capsule Endoscopy products by Given Imaging, http://www.givenimaging.com/en-int/Innovative-Solutions/Capsule-Endoscopy/Pages/default.aspx, available prior to Sep. 17, 2012.

Lehman, A.C. et al., "Surgery with Cooperative Robots," Comput. Aided. Surg., 13(2), pp. 95-105 (Mar. 2008).

Cadeddu, J.A. et al., "Novel magnetically guided intra-abdominal camera to facilitate laparoendoscopic single site surgery: initial human experience," Surg. Endoscopy, 23, pp. 1984-1899 (May 9, 2009).

C. S. Bell, K. L. Obstein, P. Valdastri, "Image partitioning and illumination in image-based pose detection for teleoperated flexible endoscopes", Artificial Intelligence in Medicine, 2013, in press.

M. Beccani, C. Di Natali, L. Sliker, J. Schoen, M. E. Rentschler, P. Valdastri, "Wireless Tissue Palpation for Intraoperative Detection of Lumps in Soft Tissue", IEEE Transactions on Biomedical Engineering, 2013, in press.

M. Simi, G. Gerboni, A. Menciassi, P. Valdastri, "Magnetic Torsion Spring Mechanism for a Wireless Biopsy Capsule", ASME Journal of Medical Devices, 2013, in press.

A. Arezzo, A. Menciassi, P. Valdastri, G. Ciuti, G. Lucarini, M. Salerno, C. Di Natali, M. Verra, P. Dario, M. Morino, "Experimental assessment of a novel robotically-driven endoscopic capsule compared to traditional colonoscopy", Digestive and Liver Disease, 2013, vol. 45, N. 8, pp. 657-662.

C. Di Natali, M. Beccani, P. Valdastri, "Real-Time Pose Detection for Magnetic Medical Devices", IEEE Transactions on Magnetics, 2013, vol. 49, N. 7, pp. 3524-3527.

M. Simi, R. Pickens, A. Menciassi, S. D. Herrell, P. Valdastri, "Fine tilt tuning of a laparoscopic camera by local magnetic actuation: Two-Port Nephrectomy Experience on Human Cadavers", Surgical Innovation, 2013, vol. 20, N. 4, pp. 385-394.

J. L. Gorlewicz, S. Battaglia, B. F. Smith, G. Ciuti, J. Gerding, A. Menciassi, K. L. Obstein, P. Valdastri, R. J. Webster III, "Wireless Insufflation of the Gastrointestinal Tract", IEEE Transactions on Biomedical Engineering, 2013, vol. 60, N. 5, pp. 1225-1233.

T. Horeman, D. D. Kurteva, P. Valdastri, F. W. Jansen, J. J. van den Dobbelsteen, J. Dankelman, "The Influence of Instrument Configuration on Tissue Handling Force in Laparoscopy", Surgical Innovation, 2013, vol. 20, N. 3, pp. 260-267.

M. Simi, M. Silvestri, C. Cavallotti, M. Vatteroni, P. Valdastri, A. Menciassi, P. Dario, "Magnetically Activated Stereoscopic Vision System for Laparoendoscopic Single Site Surgery", IEEE/ASME Transactions on Mechatronics, 2013, vol. 18, N. 3, pp. 1140-1151.

K. L. Obstein, S. Battaglia, B. F. Smith, J. S. Gerding, P. Valdastri, "Novel approach for colonic insufflation via an untethered capsule (with video)", Gastrointestinal Endoscopy, 2013, vol. 77, N. 3, pp. 516-517.

K. Obstein, P. Valdastri, "Advanced Endoscopic Technologies for Colorectal Cancer Screening", World Journal of Gastroenterology, 2013, vol. 19, N. 4, pp. 431-439.

P. Valdastri, M. Simi, R. J. Webster III, "Advanced Technologies for Gastrointestinal Endoscopy", Annual Review of Biomedical Engineering, 2012, vol. 14, pp. 397-429.

G. Ciuti, N. Pateromichelakis, M. Sfakiotakis, P. Valdastri, A. Menciassi, D. P. Tsakiris, P. Dario, "A wireless module for vibratory motor control and inertial sensing in capsule endoscopy", Sensors and Actuators A: Physical, 2012, vol. 186, pp. 270-276.

P. Valdastri, G. Ciuti, A. Verbeni, A. Menciassi, P. Dario, A. Arezzo, M. Morino, "Magnetic air capsule robotic system: Proof of concept of a novel approach for painless colonoscopy", Surgical Endoscopy, 2012, vol. 26, N. 5, pp. 1238-1246.

G. Ciuti, M. Salerno, G. Lucarini, P. Valdastri, A. Arezzo, A. Menciassi, M. Morino, P. Dario, "A Comparative Evaluation of Control Interfaces for a Robotic-Aided Endoscopic Capsule Platform", IEEE Transactions on Robotics, 2012, vol. 28, N. 2, pp. 534-538.

M. Simi, N. Tolou, P. Valdastri, J. L. Herder, A. Menciassi, P. Dario, "Modeling of a Compliant Joint in a Magnetic Levitation System for an Endoscopic Camera", Mechanical Sciences, 2012, vol. 3, pp. 5-14.

M. Salerno, G. Ciuti, G. Lucarini, R. Rizzo, P. Valdastri, A. Menciassi, A. Landi, P. Dario, "A discrete-time localization method for capsule endoscopy based on on-board magnetic sensing", Measurement Science and Technology, 2012, 23 015701 (10pp).

C. Cavallotti, P. Merlino, M. Vatteroni, P. Valdastri, A. Abramo, A. Menciassi, P. Dario, "An FPGA-based flexible demo-board for endoscopic capsule design optimization", Sensors and Actuators A: Physical, 2011, vol. 172, No. 1, pp. 301-307.

M. Silvestri, M. Simi, C. Cavallotti, M. Vatteroni, V. Ferrari, C. Freschi, P. Valdastri, A. Menciassi, P. Dario, "Comparative study on surgical performance between two- and three-dimensional vision systems and interfaces", Surgical Innovation, 2011, vol. 18, No. 3, pp. 223-230.

(56) References Cited

OTHER PUBLICATIONS

P. Valdastri, E. Sinibaldi, S. Caccavaro, G. Tortora, A. Menciassi, P. Dario, "A novel magnetic actuation system for miniature swimming robots", IEEE Transactions on Robotics, 2011, vol. 27, No. 4, pp. 769-779.

V. Pensabene, P. Valdastri, S. Tognarelli, A. Menciassi, A. Arezzo, P. Dario, "Mucoadhesive film for anchoring assistive surgical instruments in endoscopic surgery: in vivo assessment of deployment and attachment", Surgical Endoscopy, 2011, vol. 25, No. 9, pp. 3071-3079.

P. Valdastri, E. Susilo, T. Forster, C. Strohhöfer, A. Menciassi, P. Dario, "Wireless implantable electronic platform for chronic fluorescent-based biosensors", IEEE Transactions on Biomedical Engineering, 2011, vol. 58, No. 6, pp. 1846-1854.

M. Vatteroni, P. Valdastri, A. Sartori, A. Menciassi, P. Dario, "Linear-logarithmic CMOS pixel with tunable dynamic range", IEEE Transactions on Electron Devices, 2011, vol. 58, No. 4, pp. 1108-1115.

S. Tognarelli, V. Pensabene, S. Condino, P. Valdastri, A. Menciassi, A. Arezzo, P. Dario, "A pilot study on a new anchoring mechanism for surgical applications based on mucoadhesives", Minimally Invasive Therapy & Allied Technologies, 2011, vol. 20, No. 1, pp. 3-13.

M. Piccigallo, U. Scarfogliero, C. Quaglia, G. Petroni, P. Valdastri, A. Menciassi, P. Dario, "Design of a novel bimanual robotic system for single-port laparoscopy", IEEE/ASME Transactions on Mechatronics, 2010, vol. 15, No. 6, pp. 871-878.

M. Vatteroni, D. Covi, C. Cavallotti, P. Valdastri, A. Menciassi, P. Dario, A. Sartori, "Smart optical CMOS sensor for endoluminal applications", Sensors and Actuators A: Physical, 2010, vol. 162, No. 2, pp. 297-303.

D. Covi, C. Cavallotti, M. Vatteroni, L. Clementel, P. Valdastri, A. Menciassi, P. Dario, A. Sartori, "Miniaturized digital camera system for disposable endoscopic applications", Sensors and Actuators A: Physical, 2010, vol. 162, No. 2, pp. 291-296.

E. Buselli, V. Pensabene, P. Castrataro, P. Valdastri, A. Menciassi, P. Dario, "Evaluation of friction enhancement through soft polymer micro-patterns in active capsule endoscopy", Measurement Science and Technologies, 2010, 21 105802 (7pp).

P. Valdastri, C. Quaglia, E. Buselli, A. Arezzo, N. Di Lorenzo, M. Morino, A. Menciassi, P. Dario, "A Magnetic Internal Mechanism for Camera Steering in Wireless Endoluminal Applications", Endoscopy, 2010, vol. 42, pp. 481-486.

J. L. Toennies, G. Tortora, M. Simi, P. Valdastri, R. J. Webster III, "Swallowable Medical Devices for Diagnosis and Surgery: The State of the Art", Proceedings of the Institution of Mechanical Engineers, Part C: Journal of Mechanical Engineering Science, 2010, vol. 224, No. 7, pp. 1397-1414.

M. Simi, G. Ciuti, S. Tognarelli, P. Valdastri, A. Menciassi, P. Dario, "Magnetic link design for a robotic laparoscopic camera", Journal of Applied Physics, 2010, vol. 107, No. 9, pp. 09B302-09B302-3.

M. Simi, P. Valdastri, C. Quaglia, A. Menciassi, P. Dario, "Design, Fabrication and Testing of an Endocapsule with Active Hybrid Locomotion for the Exploration of the Gastrointestinal Tract", IEEE Transactions on Mechatronics, 2010, vol. 15, No. 2, pp. 170-180.

G. Ciuti, R. Donlin, P. Valdastri, A. Arezzo, A. Menciassi, M. Morino, P. Dario, "Robotic versus manual control in magnetic steering of an endoscopic capsule", Endoscopy, 2010, vol. 42, pp. 148-152.

G. Ciuti, P. Valdastri, A. Menciassi, P. Dario, "Robotic magnetic steering and locomotion of capsule endoscope for diagnostic and surgical endoluminal procedures", Robotica, 2010, vol. 28, No. 2, pp. 199-207.

R. Carta, G. Tortora, J. Thoné, B. Lenaerts, P. Valdastri, A. Menciassi, R. Puers, P. Dario, "Wireless powering for a self-propelled and steerable endoscopic capsule for stomach inspection", Biosensors and Bioelectronics, 2009, vol. 25, No. 4, pp. 845-851.

C. Quaglia, E. Buselli, R. J. Webster III, P. Valdastri, A. Menciassi, P. Dario, "An Endoscopic Capsule Robot: A Meso-Scale Engineering Case Study", Journal of Micromechanics and Microengineering, 2009, vol. 19, No. 10, 105007 (11pp).

G. Tortora, P. Valdastri, E. Susilo, A. Menciassi, P. Dario, F. Rieber, M. O. Schurr, "Propeller-based wireless device for active capsular endoscopy in the gastric district", Minimally Invasive Therapy & Allied Technologies, 2009, vol. 18, No. 5, pp. 280-290.

E. Susilo, P. Valdastri, A. Menciassi, P. Dario, "A Miniaturized Wireless Control Platform for Robotic Capsular Endoscopy Using Advanced Pseudokernel Approach", Sensors and Actuators A: Physical, 2009, vol. 156, No. 1, pp. 49-58.

C. Cavallotti, M. Piccigallo, E. Susilo, P. Valdastri, A. Menciassi, P. Dario, "An Integrated Vision System with Autofocus for Wireless Capsular Endoscopy", Sensors and Actuators A: Physical, 2009, vol. 156, No. 1, pp. 72-78.

P. Valdastri, R. J. Webster III, C. Quaglia, M. Quirini, A. Menciassi, P. Dario, "A New Mechanism for Meso-Scale Legged Locomotion in Compliant Tubular Environments", IEEE Transactions on Robotics, 2009, vol. 25, No. 5, pp. 1047-1057.

P. Valdastri, S. Tognarelli, A. Menciassi, P. Dario, "A scalable platform for biomechanical studies of tissue cutting forces", Measurement Science and Technology, 2009, vol. 20, 045801 (11pp).

E. Buselli, P. Valdastri, M. Quirini, A. Menciassi, P. Dario, "Superelastic leg design optimization for an endoscopic capsule with active locomotion", Smart Materials and Structures, 2009, vol. 18, 015001 (8pp).

P. Valdastri, C. Quaglia, E. Susilo, A. Menciassi, P. Dario, C.N. Ho, G. Anhoeck, M.O. Schurr, "Wireless Therapeutic Endoscopic Capsule: in-vivo Experiment", Endoscopy, 2008, vol. 40, pp. 979-982.

P. Valdastri, A. Menciassi, P. Dario, "Transmission Power Requirements for Novel ZigBee Implants in the Gastrointestinal Tract", IEEE Transactions on Biomedical Engineering, 2008, vol. 55, No. 6, pp. 1705-1710.

P. Valdastri, S. Rossi, A. Menciassi, V. Lionetti, F. Bernini, F. A. Recchia, P. Dario, "An Implantable ZigBee Ready Telemetric Platform for In Vivo Monitoring of Physiological Parameters", Sensors and Actuators A: Physical, 2008, vol. 142, No. 1, pp. 369-378.

A. Sieber, P. Valdastri, K. Houston, C. Eder, O. Tonet, A. Menciassi, P. Dario, "A Novel Haptic Platform for Real Time Bilateral Biomanipulation with a MEMS Sensor for Triaxial Force Feedback", Sensors and Actuators A: Physical, 2008, vol. 142, No. 1, pp. 19-27.

A. Sieber, P. Valdastri, K. Houston, A. Menciassi, P. Dario, "Flip Chip Microassembly of a Silicon Triaxial Force Sensor on Flexible Substrates", Sensors and Actuators A: Physical, 2008, vol. 142, No. 1, pp. 421-428.

L. Beccai, S. Roccella, L. Ascari, P. Valdastri, A. Sieber, M. C. Carrozza, P. Dario, "Development and Experimental Analysis of a Soft Compliant Tactile Microsensor to be Integrated in an Antropomorphic Artificial Hand", IEEE/ASME Transactions on Mechatronics, 2008, vol. 13, No. 2, pp. 158-168.

C. Oddo, P. Valdastri, L. Beccai, S. Roccella, M.C. Carrozza, P. Dario, "Investigation on calibration methods for multi-axis, linear and redundant force sensors", Measurement Science and Technology, 2007, vol. 18, pp. 623-631.

P. Valdastri, K. Houston, A. Menciassi, P. Dario, A. Sieber, M. Yanagihara, M. Fujie, "Miniaturised Cutting Tool with Triaxial Force Sensing Capabilities for Minimally Invasive Surgery", ASME Journal of Medical Devices, 2007, vol. 1, N. 3, pp. 206-211.

G. Turchetti, B. Labella, P. Valdastri, A. Menciassi, P. Dario, "The importance of giving an alternative: the case of fetal surgery", Int. J. Healthcare Technology and Management, 2007, vol. 8, Nos. 3-4, pp. 250-267.

P. Valdastri, K. Harada, A. Menciassi, L. Beccai, C. Stefanini, M. Fujie, and P. Dario, "Integration of a Miniaturised Triaxial Force Sensor in a Minimally Invasive Surgical Tool", IEEE Transactions on Biomedical Engineering, 2006, vol. 53, No. 11, 2397-2400.

P. Valdastri, P. Corradi, A. Menciassi, T. Schmickl, K. Crailsheim, J. Seyfried, P. Dario, "Micromanipulation, Communication and Swarm Intelligence Issues in a Swarm Microrobotic Platform", Robotics and Autonomous Systems, 2006, vol. 54, No. 10, pp. 789-804.

(56) References Cited

OTHER PUBLICATIONS

P. Valdastri, S. Roccella, L. Beccai, E. Cattin, A. Menciassi, M. C. Carrozza, P. Dario, "Characterization of a novel hybrid silicon three-axial force sensor", Sensors and Actuators A: Physical, 2005, vol. 123-124C, pp. 249-257.

L. Beccai, S. Roccella, A. Arena, F. Valvo, P. Valdastri, A. Menciassi, M. C. Carrozza, P. Dario, "Design and fabrication of a hybrid silicon three axial force sensor for biomechanical applications", Sensors and Actuators A: Physical, 2005, vol. 120, No. 2, pp. 370-382.

P. Valdastri, A. Menciassi, A. Arena, C. Caccamo, and P. Dario, "An Implantable Telemetry Platform System for in vivo Monitoring of Physiological Parameters", IEEE Transactions on Information Technology in Biomedicine, 2004, vol. 8, No. 3, pp. 271-278.

X. Wang, C. Di Natali, M. Beccani, M. Kern, P. Valdastri, M. Rentschler, "Novel Medical Wired Palpation Device: A Device Validation Study of Material Properties", Transducers 2013, Barcelona, Spain, pp. 1653-1658.

M. Beccani, C. Di Natali, M. E. Rentschler, P. Valdastri, "Wireless Tissue Palpation: Proof of Concept for a Single Degree of Freedom", IEEE International Conference on Robotics and Automation (ICRA) 2013, Karlsruhe, Germany, pp. 703-709.

M. Beccani, C. Di Natali, M. Rentschler, P. Valdastri, "Uniaxial Wireless Tissue Palpation Device for Minimally Invasive Surgery", ASME Design of Medical Devices Conference, Apr. 2013, Minneapolis, Minnesota, ASME Journal of Medical Devices, vol. 7, N. 2, 020919 (3 pp).

C. Di Natali, P. Valdastri "Remote active magnetic actuation for a single-access surgical robotic manipulator", in Proc. of the XVI Annual Conference of the International Society for Computer Aided Surgery (ISCAS) 2012, Pisa, Italy, Jun. 2012, International Journal of Computer Assisted Radiology and Surgery, 2012, vol. 7, Suppl. 1, pp. S169-S170.

C. Di Natali, T. Ranzani, M. Simi, A. Menciassi, P. Valdastri "Trans-abdominal Active Magnetic Linkage for Robotic Surgery: Concept Definition and Model Assessment", in Proc. of IEEE International Conference on Robotics and Automation (ICRA) 2012, St Paul, MN, USA, May 2012, pp. 695-700.

M. Simi, G. Gerboni, A. Menciassi, P. Valdastri, "Magnetic Mechanism for Wireless Capsule Biopsy", in Proc. of ASME Design of Medical Devices Conference, Apr. 10-12, 2012, Minneapolis, MN, ASME Journal of Medical Devices, vol. 6, p. 017611-1.

T. Ranzani, C. Di Natali, M. Simi, A. Menciassi, P. Dario, P. Valdastri, "A Novel Surgical Robotic Platform Minimizing Access Trauma", in Proc. of 4th Hamlyn Symposium on Medical Robotics, London, UK, Jun. 2011, pp. 15-16.

P. Valdastri, G. Ciuti, A. Verbeni, A. Menciassi, P. Dario, A. Arezzo, M. Morino, "Magnetic air capsule robotic system: a novel approach for painless colonoscopy", 19th International Congress of the European Association of Endoscopic Surgery (EAES) in Turin, Italy.

M. Simi, G. Sardi, P. Valdastri, A. Menciassi, P. Dario, "Magnetic Levitation Camera Robot for Endoscopic Surgery", in Proc. of IEEE International Conference on Robotics and Automation (ICRA) 2011, Shanghai, China, May 2011, pp. 5279-5284.

O. Alonso, J. Canals, L. Freixas, J. Samitier, A. Dieguez, M. Vatteroni, E. Susilo, C. Cavallotti, P. Valdastri, "Enabling multiple robotic functions in an endoscopic capsule for the entire gastrointestinal tract exploration", in Proc. ESSCIRC, 2010, pp. 386-389.

J. L. Toennies, G. Ciuti, B. F. Smith, A. Menciassi, P. Valdastri, and Robert J. Webster III, "Toward Tetherless Insufflation of the GI Tract", in Proc. IEEE Engineering in Medicine and Biology Society Conference (EMBC) 2010, Buenos Aires, Argentina, Sep. 2010, pp. 1946-1949.

G. Tortora, S. Caccavaro, P. Valdastri, A. Menciassi, P. Dario, "Design of an autonomous jellyfish miniature robot based on a novel concept of magnetic actuation", in Proc. of IEEE International Conference on Robotics and Automation (ICRA) 2010, Anchorage, AK, USA, May 2010, pp. 1592-1597.

L. S. Chiang, P. S. Jay, P. Valdastri, A. Menciassi, P. Dario, "Tendon Sheath Analysis for Prediction of Distal End Force and Elongation", in Proc. IEEE/ASME Conference on Advanced Intelligent Mechatronics 2009, Singapore, Jul. 2009, pp. 332-337.

O. Tonet, M. Marinelli, G. Megali, A. Sieber, P. Valdastri, A. Menciassi, P. Dario, "Control of a teleoperated nanomanipulator with time delay under direct vision feedback", in Proc. of IEEE International Conference on Robotics and Automation (ICRA) 2007, Rome, Italy, Apr. 2007, pp. 3514-3519.

J. L. Toennies, R. J. Webster III, P. Valdastri, "Mesoscale Mobile Robots for Gastrointestinal Minimally Invasive Surgery (MIS)", Chapter 10, pp. 224-251, in "Medical Robotics—Minimally Invasive Surgery" edited by Paula Gomes, Woodhead Publishing Series in Biomaterials: No. 51, ISBN 0-85709-130-1 (Aug. 2012).

A. Menciassi, P. Valdastri, K. Harada, P. Dario, "Single and Multiple Robotic Capsules for Endoluminal Diagnosis and Surgery", Chapter 14, pp. 313-354, in "Surgical Robotics—System Applications and Visions", edited by J. Rosen, B. Hannaford, R. Satava, published by Springer, 1st Edition, 2011, XXII, 819 p. 365 illus, Hardcover, ISBN: 978-1-4419-1125-4.

B. Laulicht, N. Gidmark, A. Tripathl, E. Mathiowitz, "Localization of magnetic pills," Proc. of the National Academy of Sciences, vol. 108, No. 6, 2252-2257 (Feb. 8, 2011).

PCT International Search Report and Written Opinion for Application No. PCT/US2014/012086 dated May 14, 2014.

PCT International Search Report and Written Opinion for Application No. PCT/IB2012/052739 dated Aug. 7, 2012.

"S. Best, E. Olweny, S. Park, P. Smith, R. Fernandez, D. Scott, R. Bergs, and J. Cadeddu. Newgeneration magnetic camera facilitates porcine LESS nephrectomy. The Journal of Urology, 185:e413-e413, 2011."

U.S. Office action for U.S. Appl. No. 14/027,561 dated Jun. 23, 2015.

* cited by examiner

SYSTEM AND METHOD FOR DETECTING TISSUE SURFACE PROPERTIES

RELATED APPLICATIONS

This application is a nonprovisional of and claims the benefit of U.S. Provisional Patent Application No. 61/803,700, filed on Mar. 20, 2013. This application also claims priority to U.S. patent application Ser. No. 14/027,561, filed on Sep. 16, 2013, which claims the benefit of U.S. Provisional Patent Application No. 61/701,447, filed on Sep. 14, 2012. The entire contents of each of these applications are incorporated herein by reference.

BACKGROUND OF THE INVENTION

Palpation is commonly used in open surgery to manually detect tissue abnormalities. Manual palpation typically requires open surgery with large incisions, and therefore longer recovery times for the patient. During open surgery, surgeons use their hands to access the anatomy and to feel their way around sensitive anatomical structures and to correlate the actual anatomy with preoperative data. Examples where surgeons employ manual palpation include identification of underlying arteries during dissection, identification of hepatic aneurysms during liver surgery, intramedullary fixation of tibia and femur during orthopedic surgery, assistance during adenoidectomy procedures, and identification of laryngeal nerves during thyroid surgery. Additional examples includes surgeons using manual palpation to search for abnormalities such as breast masses, cancer, heart and liver enlargement, to identify active ulcers, and to localize aneurysms.

Manual palpation capabilities are unfortunately lost during minimally invasive surgery ("MIS"), which has many other advantages such as trauma reduction, improved cosmesis, shortened recovery time, and reduced hospitalization costs.

Some devices that restore palpation feedback have been proposed for MIS, but none of them have been translated to clinical application thus far. One of the main reasons is that devoting one of the few abdominal access ports in a minimally invasive procedure to an instrument that tries to restore palpation has never been considered to be a wise investment for the sake of surgical outcomes. Despite progress in robotic assistance, existing MIS robotic systems do not support palpation, and they are predominantly passive "motion replicators" (i.e., the robot grippers follow direct or scaled motions of the surgeon's hands). To date, there are no algorithms that enable robots to use in-vivo sensory palpation data to actively augment the surgeon's perception of the surgical field or assist in in vivo diagnostics and in task execution. Also, from a design perspective, existing robotic MIS systems are increasingly able to restore dexterous surgical intervention capabilities typically available to surgeons during open surgery. These systems however, are limited by both physical designs and by their control algorithms. Design limitations restrict their use to trans-cutaneous access in bodily cavities by using 3-5 access ports while having a physical connection to extracorporeal actuation devices, which limit end-effector travel within the patient's body.

A wireless palpation technique would not consume port space and can be used beyond minimally invasive surgery, whenever the proposed invention can be introduced by natural orifices or tiny incisions.

SUMMARY OF THE INVENTION

The present invention relates to systems and methods for providing clinicians with haptic feedback during minimally invasive surgery ("MIS"). In particular, the present invention relates to detecting and assessing a tissue surface property without a separate access port to internal structures.

The present invention relates to a wireless palpation device ("WPD") which provides a novel approach to detecting underlying tissue abnormalities. By way of example, the present invention may be used in colorectal cancer detection, detection of abnormalities in the GI tract, and detection of abnormalities in abdominal organs during MIS.

The present invention includes two units: a first unit positioned outside the patient's body and a second unit positioned inside the patient's body. The first unit includes a magnetic field source and a force sensor and is positioned outside the patient's body in a position that enables magnetic coupling with the second unit, which is inside the patient's body. The second unit includes a magnetic field source and other components, and thereby the resulting attractive force between the magnetic field sources can be perceived by the force sensor of the first unit. By varying the distance between the two units, the attractive force triggers a variable stress on the tissue surrounding the second unit in the direction of the magnetic field source in the first unit.

In one embodiment, the invention provides a system for detecting a tissue property. The system includes a first or outer unit located on a first side of the tissue surface. The first unit includes a housing have a sensor and a magnetic field source. The system also includes a second or inner unit located on a second side of the tissue surface. The second unit includes a housing that supports at least one sensor, a magnetic field source, a controller, a telemetry unit, and a power source. The first unit is magnetically coupled to the second unit such that a force created therebetween triggers stress on the tissue surface. The sensor in the first unit determines a magnitude of the force between the first and second units, while the sensor in the second unit determines displacement of the tissue surface that results from the force.

In another embodiment, the invention provides a system for detecting a tissue property. The system includes a first unit positioned exterior to a patient and a second unit positioned inside of the patient near a target tissue. The first unit includes a first housing, a first sensor supported by the first housing, and a first magnetic field source supported by the housing. The second unit includes a second housing, a second sensor supported by the second housing, the second sensor positioned adjacent the target tissue, a second magnetic field source supported by the second housing, a controller supported by the second housing, a telemetry unit supported by the second housing, and a power source supported by the second housing. The first sensor is configured to detect an amount of force applied to the target tissue due to a magnetic coupling between the first unit and the second unit, and the second sensor is configured to determine a displacement of the tissue due to the magnetic coupling between the first unit and the second unit.

In a further embodiment, the invention provides a method for detecting a tissue surface contour. The method includes the steps of positioning, using a trocar, a first unit on a first side of the tissue surface at a region of interest. The first unit includes a housing that supports at least one sensor, a magnetic field source, a controller, a telemetry unit, and a power source. The method further includes providing a second unit on a second side of the tissue surface. The second unit includes a housing having a sensor and a magnetic field source. The method also includes modulating a force created by a magnetic field between the first and second units in order to determine and monitor displacement of the tissue surface resulting from the force.

In yet another embodiment, the invention provides a system for detecting a tissue property. The system comprises a first unit positioned outside a patient body and a second unit positioned inside the patient's body. The first unit includes a first housing, and a magnetic field source supported by the first housing. The second unit includes a second housing, a pressure sensor supported by the second housing, a localization module supported by the second housing, a controller, and a power source. The pressure sensor is configured to detect an indentation force applied to the tissue, and the second unit is configured to wirelessly transmit the indentation force data and localization data to a computer to generate a volumetric stiffness map for the tissue.

In a further embodiment, the invention provides a device insertable through an incision in a human body to determine tissue stiffness. The device comprises an enclosed housing having a first end and a second end, a pressure sensor positioned at the first end of the housing, a localization module supported within the enclosed housing, a controller supported within the enclosed housing, and a power source supported within the enclosed housing and configured to provide power to the controller. The pressure sensor is configured to detect an indentation force applied to the tissue. The localization module is configured to determine a position of the housing relative to a magnetic field source when the indentation force is applied to the tissue. The controller is configured to wirelessly transmit the indentation force data and the localization data to a computer to generate a volumetric stiffness map for the tissue.

In another embodiment, the invention provides a method for detecting a tissue property. The method comprises positioning a first unit outside of a patient body near a region of interest, the first unit including a first housing that supports a magnetic field source, positioning a second unit inside the patient body at the region of interest, the second unit including a second housing that supports a pressure sensor, a plurality of magnetic field sensors, and an inertial sensor, applying pressure on the region of interest with the second unit, determining a tissue reaction pressure based on the pressure applied to the region of interest, determining an indentation depth of the tissue when the pressure is applied to the region of interest, determining a position of the second unit when the pressure is applied to the region of interest, wirelessly transmitting the tissue reaction pressure and the position data to a computer, and generating a tissue stiffness map based on the tissue reaction pressure, the tissue indentation depth, and the position of the second unit.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The invention relates to systems and devices for detecting tissue properties and abnormalities. The systems and devices disclosed provide two approaches to restoring palpation in MIS and robotic MIS to, for example, identify precise margins for curative tumor resections. The first system and device described herein is the robot driven wireless palpation approach, and the second system and device described herein is the surgeon driven wireless palpation approach.

Robot Driven Wireless Palpation System

Figure 1:
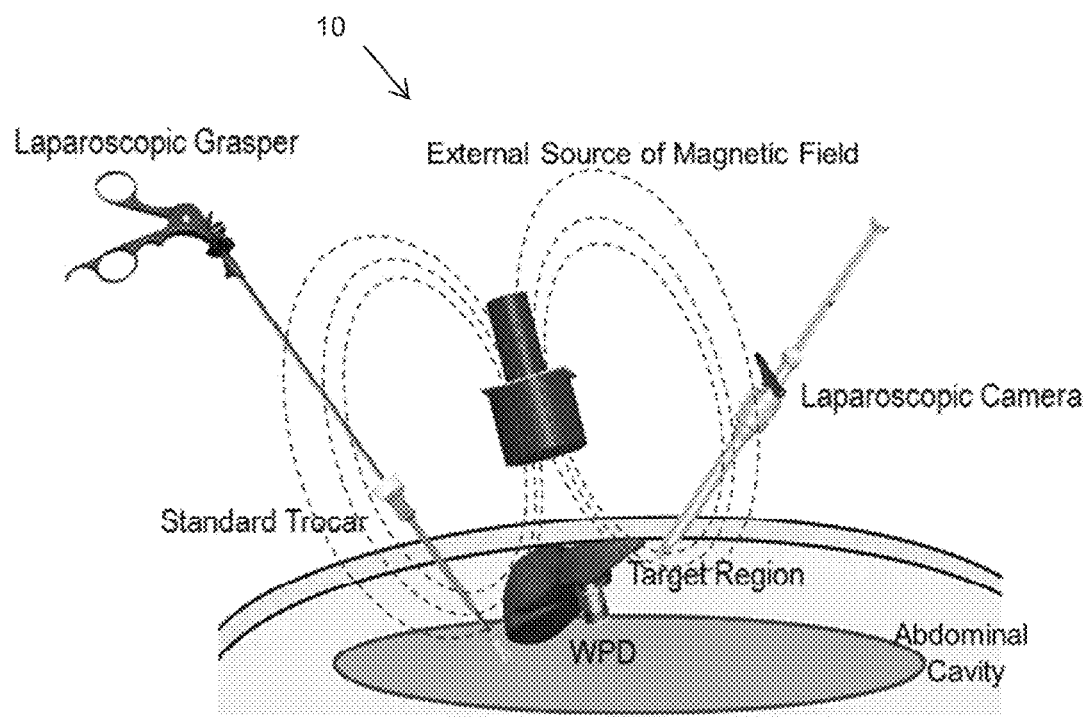
FIG. 1 illustrates a system for detecting tissue surface properties according to an embodiment of the present invention.
Figure 2:
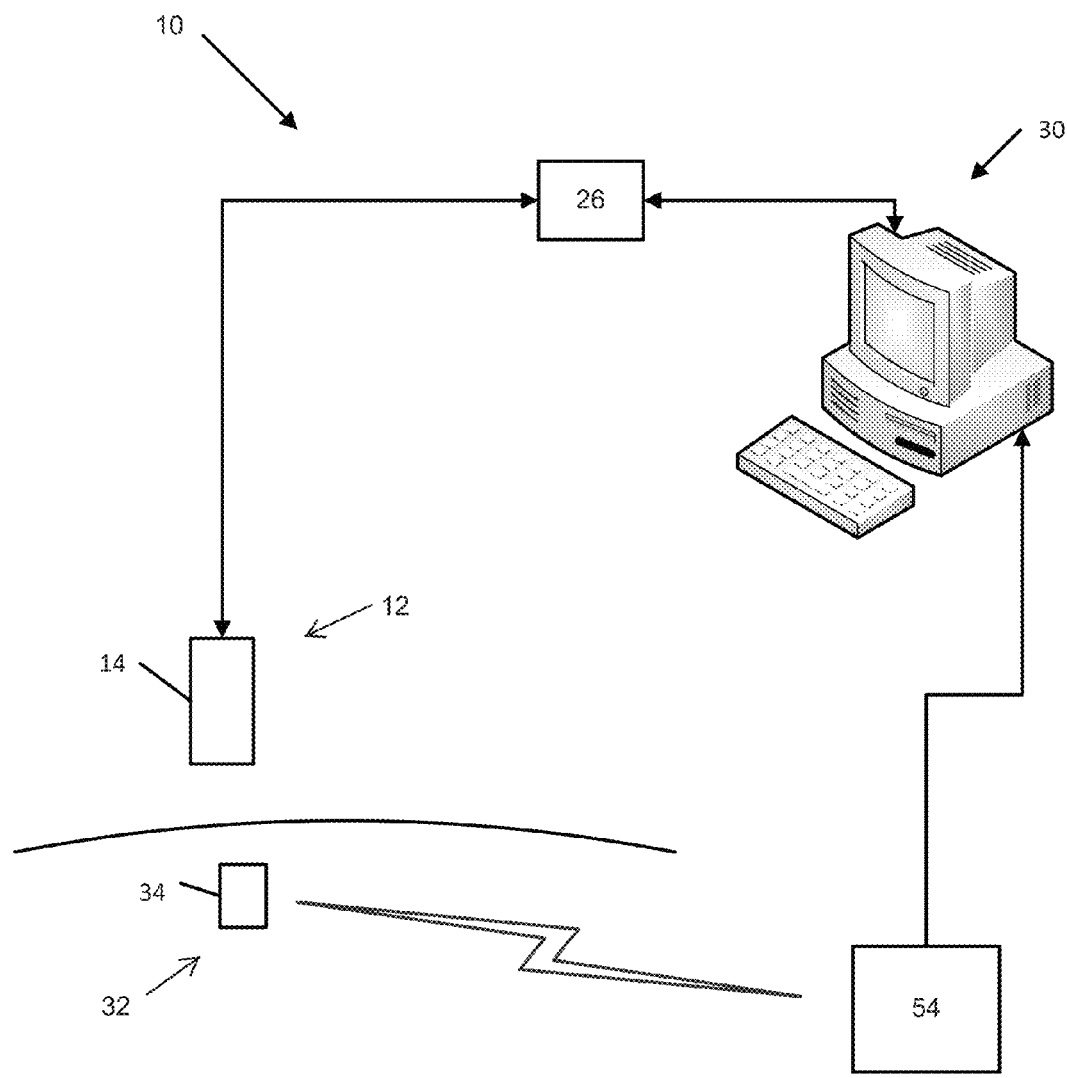
FIG. 2 is a schematic view of the system for detecting tissue surface properties illustrated in FIG. 1.

FIGS. 1-2 illustrate a system 10 for detecting tissue surface properties according to an embodiment of the present invention. For example, the system 10 can determine a tissue surface property related to local mechanical stiffness. For small indentation depths (10% of tissue thickness), it can be assumed that the tissue is linear elastic and represents the local tissue stiffness as a function of tissue reaction force and indentation depth. Since cancer tissue is stiffer than healthy tissue, the system 10 generates a stiffness map that indicates to the surgeon the location of the tumor (e.g., a region that is stiffer than the surroundings) and its boundaries.

The system 10 includes a first device 12 having a first housing 14 positioned outside of a patient's body. The first housing 14 supports a magnetic field source 18 and a sensor 22 (e.g., force sensor). The sensor 22 can be positioned at an end of the first housing 14 that would contact the tissue. The sensor 22 can be in communication (via hardwire connection or wirelessly) with a computer program 26 configured to receive signals representing magnitude of force data from the force sensor 22. The computer program 26 when operated by a computer or processor 30 can process or compute a relevant output for presentation on a display or computer monitor. The output can represent a local stiffness map that would identify stiffer regions on the organ surface.

Figure 3:
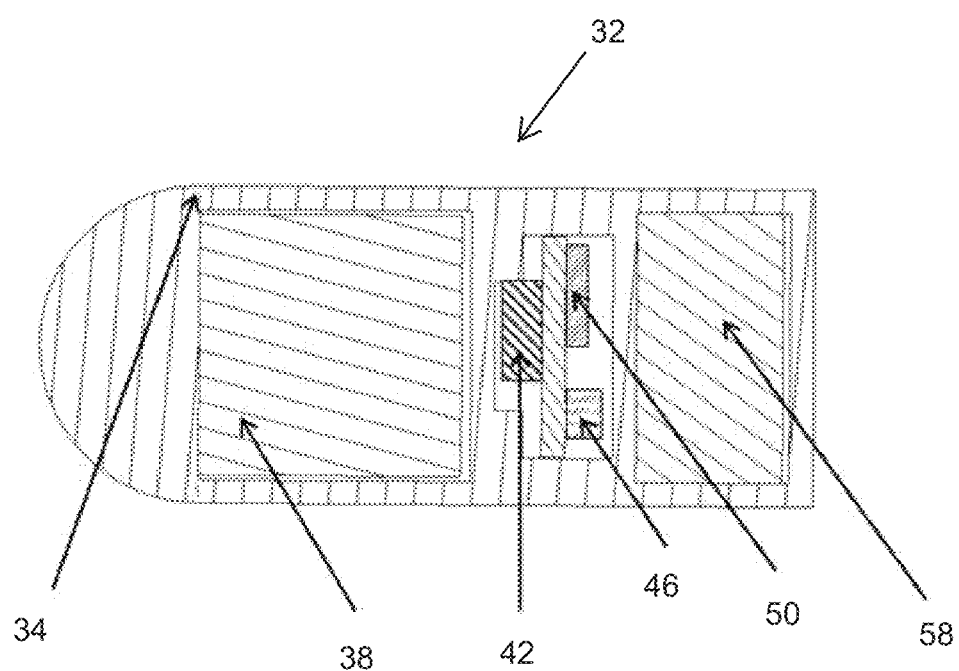
FIG. 3 is a schematic view of a device in the system illustrated in FIGS. 1-2.

The system 10 also includes a second device 32 having a housing 34 configured for positioning inside the patient's body near a target location. With additional reference to FIG. 3, the second housing 34 supports a magnetic field source 38 (e.g., a permanent magnet), a processor or microcontroller 42, one or more sensors 46 (e.g., magnetic field sensor, a magnetometer, inertial sensor, contact sensor), a wireless telemetry unit 50 (e.g., a wireless transceiver) configured to transmit signals representing compression displacement data from the processor 42 to a receiver 54, and a power source 58 (e.g., a rechargeable battery). The receiver 54 is capable of receiving the signals from the wireless telemetry unit 50, and can further communicate the signals to the computer 30 for input to the computer program 26 (or other computer program), additional processing by the computer, and/or presentation on a display or computer monitor. For example, the output presented can be a stiffness topographical map.

Figure 4:
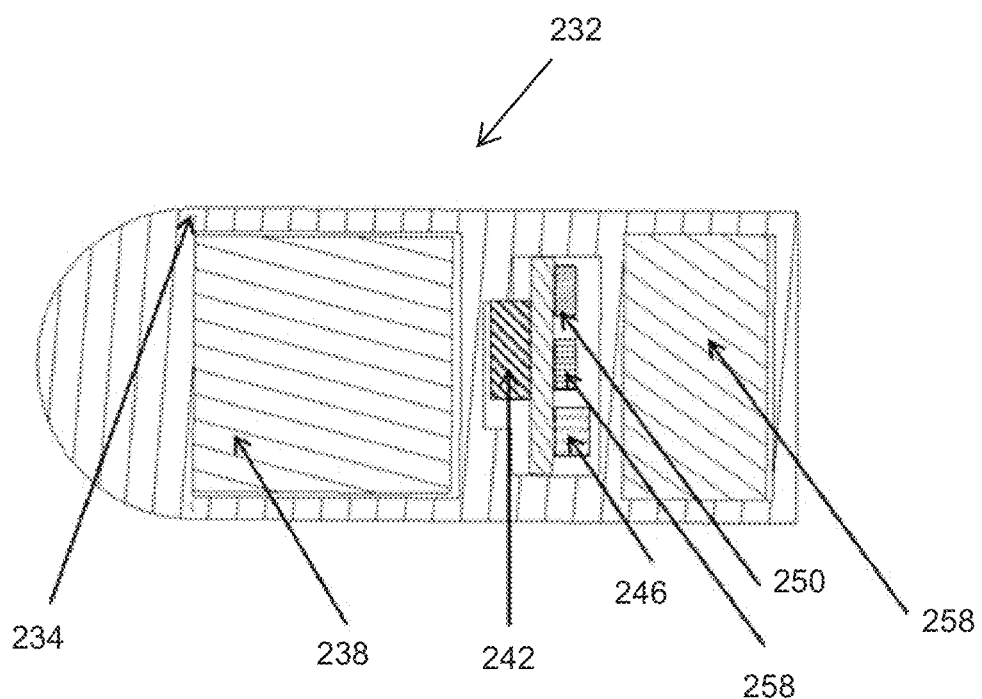
FIG. 4 is a schematic view of a device in the system illustrated in FIGS. 1-3.

FIG. 4 illustrates an alternate construction of the second device 32 (referred to as 232). The second housing 234 includes a magnetic field source 238 (e.g., a permanent magnet), a processor or microcontroller 242, one or more sensors 246 (e.g., magnetic field sensor, a Hall Effect transducer), a wireless telemetry unit 250 (e.g., a wireless transceiver) configured to transmit signals representing force data from inside the patient to the first housing 14, a power source 258 (e.g., a rechargeable battery), and one or more actuators 258 (e.g., a DC motor) configured to produce different kind of stresses on the tissue combining the attractive force between the two magnetic sources with other forces.

Figure 5:
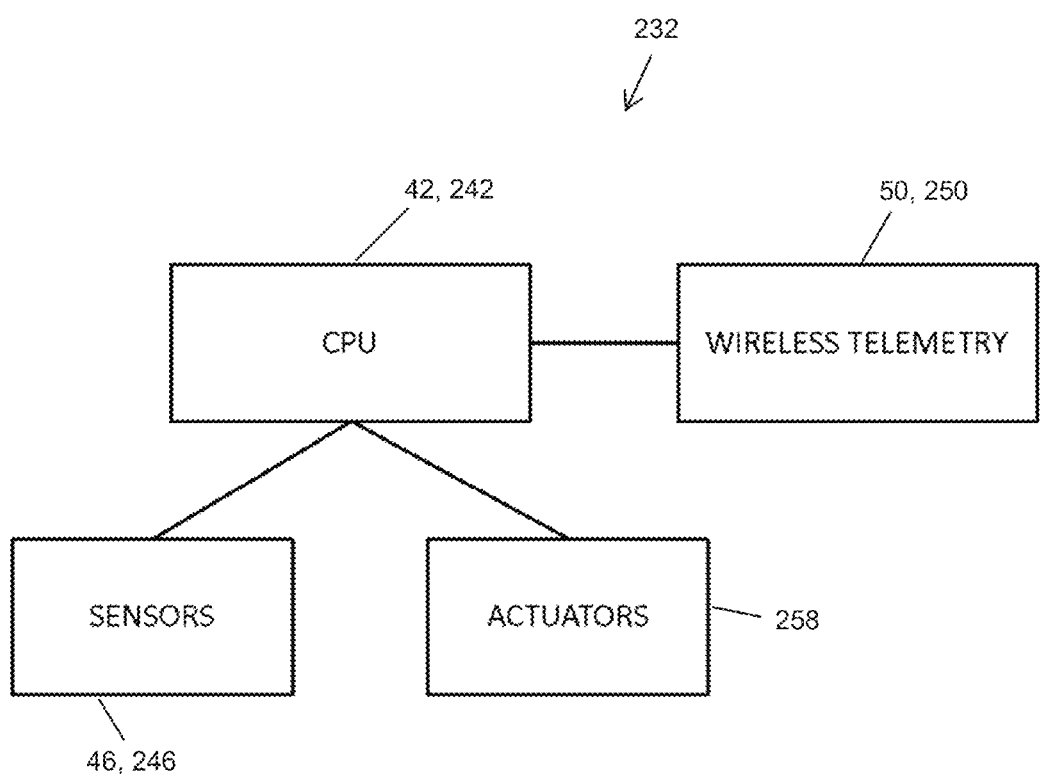
FIG. 5 is a schematic view of a device in the system illustrated in FIGS. 1-4.

FIG. 5 schematically illustrates the components supported by the second housing 234. The one or more sensors 246 and the one or more actuators 258 are in communication with the processor 242 and provide signals representing force data to the processor 242. The processor 242, which is in communication with the wireless telemetry unit 250, transmits the data from the sensors 246 and actuators 258 to the wireless telemetry unit 250 for output to a receiver 54 capable of receiving the data. As noted above, the receiver 54 is capable of receiving data from the wireless telemetry unit 50, and can further communicate the data to the computer 30 for input to the computer program 26 (or other computer program), additional processing by the computer, and/or presentation on a display or computer monitor.

Figure 6:
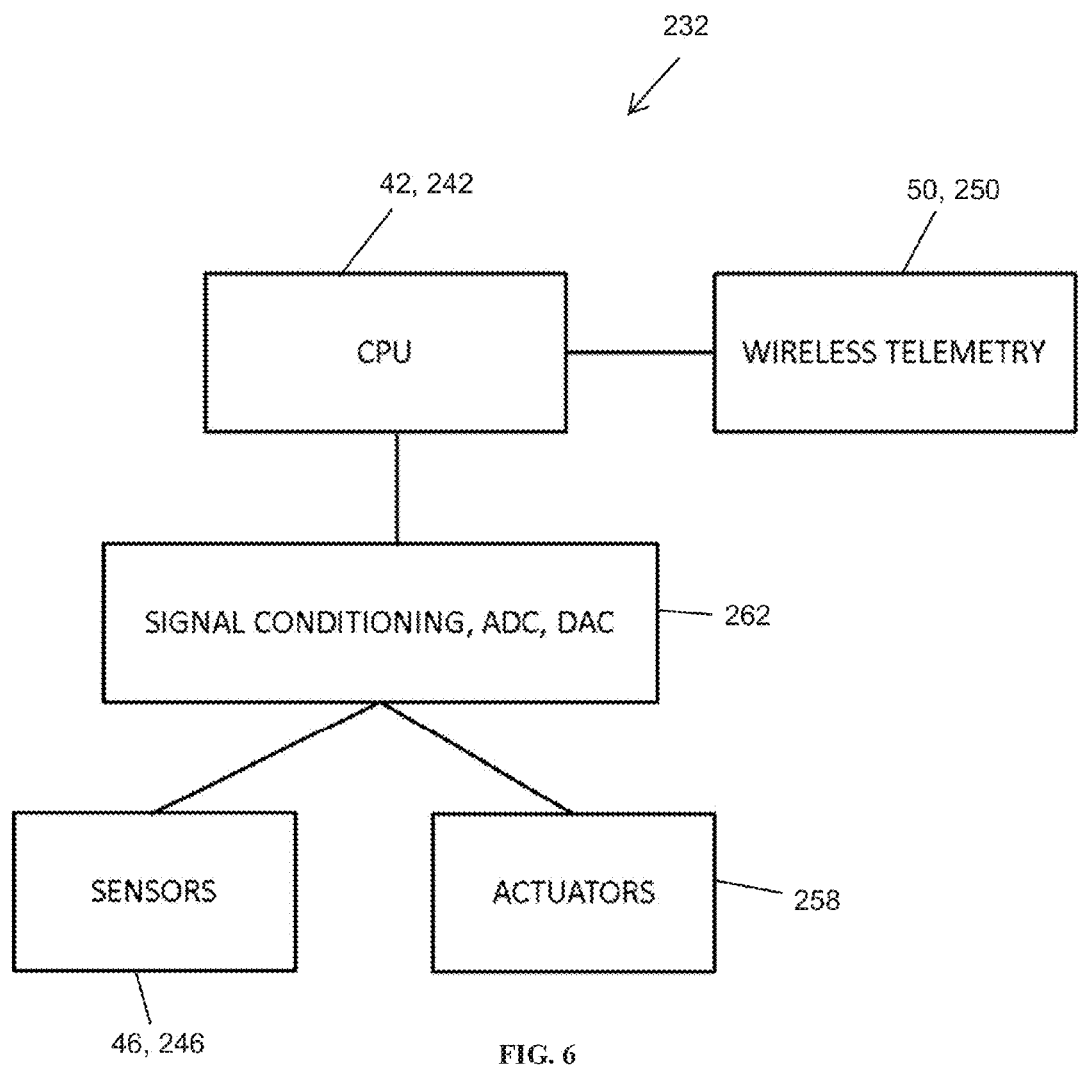
FIG. 6 is a schematic view of a device in the system illustrated in FIGS. 1-5.

FIG. 6 illustrates an additional component 262 that may be employed in the second housing 234. The additional component 262 includes a signal conditioning unit such as an analog-to-digital converter or a digital-to-analog converter. In this construction, the signal conditioning unit 262 receives the signals from the sensors 246 and actuators 258 and conditions those signals before transmitting them to the processor 242

Figure 7:
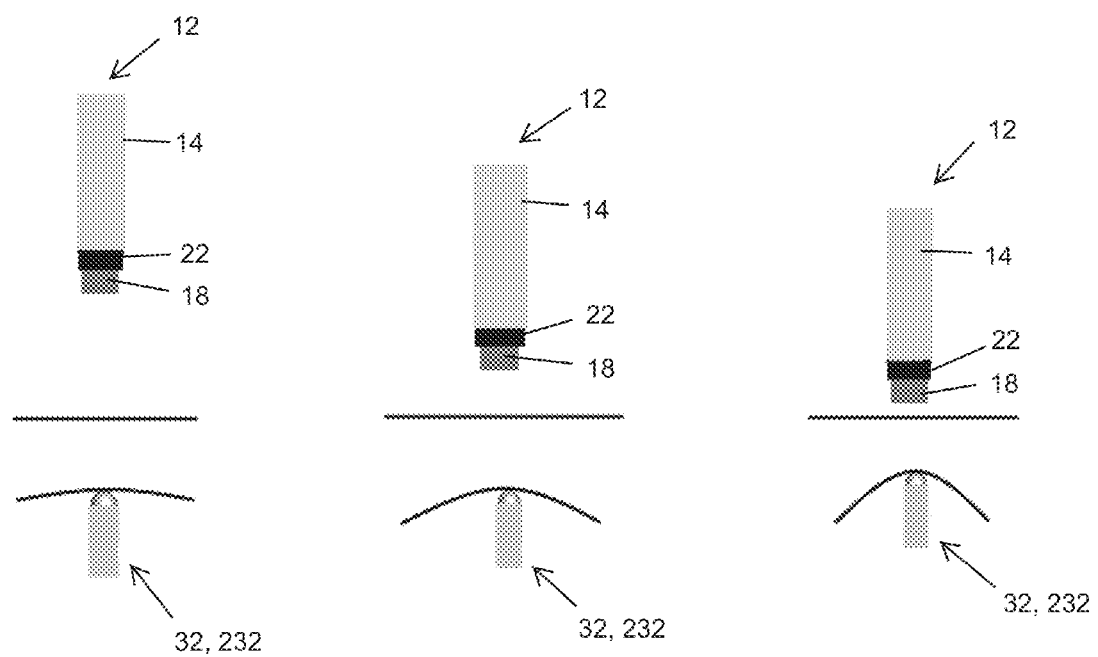
FIG. 7 is a schematic view of the system in operation.

With reference to FIGS. 7A-C, the system 10 operates to magnetically couple the magnetic field source 18 in the first housing 14 with the magnetic field source 38 of the second housing 34. The resulting attractive magnetic force between the two magnetic sources 18, 38 can be perceived by the force sensor 22 in the first housing 14. By varying the distance between the first housing 14 and the second housing 34, the attractive force triggers a variable stress up on the tissue surrounding the second housing 34 in the direction of the external magnetic field source 18. As illustrated in FIGS. 7A-C, as the user moves the first housing 14 closer to the housing 34, the tissue experiences a different amount of stress. The resulting stress on the tissue under test is a function of the distance between the two magnetic sources, i.e., the closer the first housing 14 is with respect to the second housing 34 the greater the resulting compression stress is on the tissue. In addition, the one or more sensors 46 in the second housing 34 detect a compression displacement of the tissue due to the magnetic force variation. Because of the wireless telemetry unit 50 (or 250) embedded in the second housing 34 (or 234), the acquired data can be transmitted in real time remotely, and therefore, tissue properties can be determined.

As noted above, MIS has become popular due to the benefits of patient recovery time, less pain, and less scarring. Robotic MIS also suffers from the drawbacks discussed above since haptic feedback is not available to the surgeon because robotic surgical instruments are teleoperated from a remote console. Therefore in both MIS and robotic MIS, the surgeon is not able to leverage tactile and kinesthetic sensations to prevent accidental tissue damage or to explore tissue and organ features by palpation.

Prior research toward restoring tactile and kinesthetic sensations in MIS has focused on the distal sensing element or on the proximal rendering of haptic cues, always requiring a dedicated insertion port for the instrument. But, because surgeons do not appear willing to devote one surgical port to an instrument whose only purpose is to palpate tissues, a commercially viable solution has not been implemented. The inventors have found that having a tissue indenter (for measuring indentation pressure of the tissue using a pressure sensor) that does not take up port space may overcome this potential barrier. The inventors proposed solution to this challenge is the system 10 described above.

The inventors carried out a pilot study to assess the feasibility of wireless tissue palpation, where a magnetic device is deployed through a standard surgical trocar and operated to perform tissue palpation without requiring a dedicated entry port. The pilot study is described below.

The proposed platform used in the pilot study is composed of a wireless palpation device and a robotic manipulator holding a load cell and a permanent magnet. The wireless device included a sensing module, a wireless microcontroller, a battery, and a permanent magnet housed in a cylindrical shell (about 12.7 mm in diameter and about 27.5 mm in height). This preliminary study assessed the precision in reconstructing the indentation depth leveraging on magnetic field measurements at the wireless device (i.e., 0.1 mm accuracy), and demonstrated the effectiveness of wireless vertical indentation in detecting the elastic modulus of three different silicone tissue simulators (elastic modulus ranging from 50 kPa to 93 kPa), showing a maximum relative error below 3%. Finally, wireless palpation was used to identify differences in tissue stiffness due to a spherical lump embedded into a porcine liver. The reported results have the potential to open a new research stream in the field of palpation devices, where direct physical connection across the abdominal wall is no longer required.

Materials

A. Principle of Operation

With reference to FIG. 1, an external source of magnetic field and a wireless palpation device (WPD), which included a miniature permanent magnet and wireless electronics. The WPD was introduced into the abdominal cavity through a standard trocar and positioned on the target by a laparoscopic grasper. Then, tissue indentation was obtained by properly modulating the gradient of the external magnetic field. In order to generate kinesthetic data, the indentation depth and the pressure applied on the tissue must be known at any given time. In this pilot study, the inventors restricted the investigation to a single degree of freedom (i.e., vertical indentation) as a first step toward proving the feasibility of the proposed approach.

Figure 8:
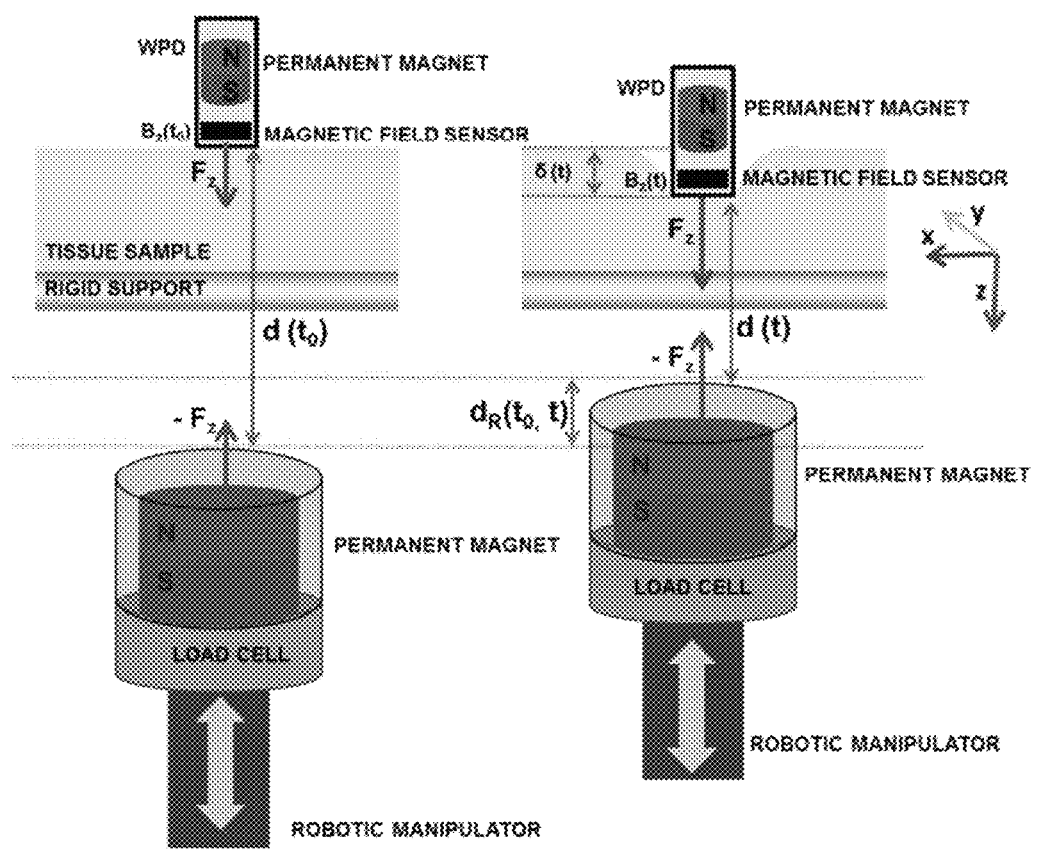
FIG. 8 is a schematic diagram of a test platform of the system used in a study.

A permanent magnet mounted at the end effector of a robotic manipulator was adopted as an external source of magnetic field. Considering the two magnets (i.e., the one inside the WPD and the one at the external manipulator) oriented as in FIG. 8, the inventors studied the indentation of a tissue sample along the vertical direction by cyclically translating the external magnet along the Z axis. Neglecting gravity and assuming a pure vertical motion for the WPD, the pressure exerted on the tissue was provided by the ratio of the intermagnetic force along the Z axis, $F_z$, and the area of the WPD face in contact with the tissue. At equilibrium, the intensity of $F_z$ was measured by placing a load cell in between the external permanent magnet and the end effector of the manipulator. For vertical indentation as represented in FIG. 8, gravity force acting on the WPD was considered as a preload on the tissue and factored out as an offset in the indentation trial. For any other configuration, an accelerometer can be embedded in the WPD to provide the inclination, thus allowing quantification of the exact contribution of the gravity force, should this vary during indentation. In this study, the inertial sensor was mainly used to verify the assumption of pure vertical motion for the WPD. The indentation depth $\delta(t)$ was evaluated by measuring the Z component of the magnetic field at the WPD. In particular, referring to FIG. 8 and focusing on the tissue loading phase, it is possible to express the distance between the external magnet and the internal magnet at the generic instant t as:

$$d(t)=d(t_0)-\delta(t)-d_R(t_0,t) \qquad \text{Eq. 1}$$

where $d_R(t_0, t)$ is the vertical distance traveled by the robotic manipulator since the beginning of the loading phase occurred in $t_0$. Since the motion of the external magnet is limited to the Z axis and the WPD is aligned on that same direction in virtue of magnetic coupling, we assumed that the Z component of the magnetic field at the WPD, $B_Z(t)$, is an univocal function of d(t):

$$B_Z(t)=\Phi[d(t)] \qquad \text{Eq. 2}$$

that can be numerically quantified through experimental calibration. Therefore, the indentation depth $\delta(t)$ can be expressed by merging Eq. 2 with Eq. 1 and rearranging the terms as:

$$\delta(t)=\Phi[B_Z(t_0)]^{-1}-\Phi[B_Z(t)]^{-1}-d_R(t_0,t) \qquad \text{Eq. 3}$$

Since the value of $d_R(t_0,t)$ is available at any given time from the manipulator encoders and $B_Z(t)$ can be measured by placing a Hall effect sensor in the WPD, the total indentation depth can be computed at any given time during the loading phase. Same mathematical formulation applies—mutatis mutandis—to the tissue unloading phase.

A relevant assumption for the proposed approach consists in considering all the tissue deformation occurring at the interface with the WPD. This holds true for the schematization represented in FIG. 8—where the tissue under test is laying on a rigid support. However, it may not be valid as well in in vivo conditions, where the organ may lay on a softer tissue. This approximation is well accepted in the field of in vivo tissue indentation, as long as the indentation depth is relatively smaller (at least 10%) than the thickness of the organ under test.

B. Experimental Platform Overview

Figure 9:
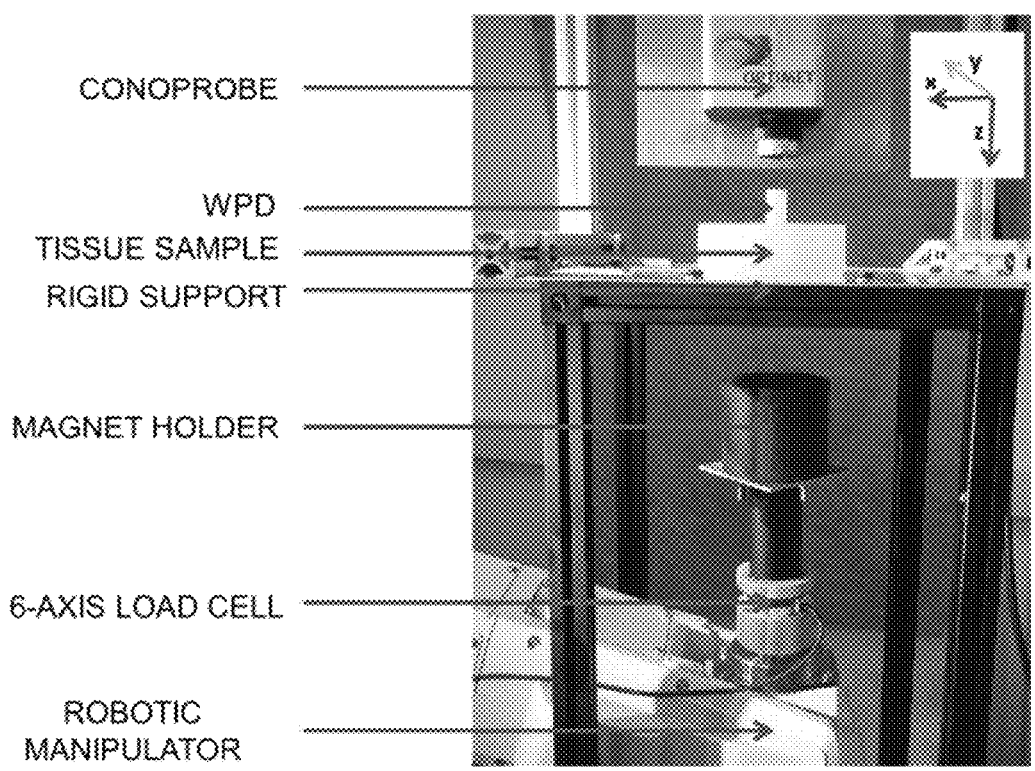
FIG. 9 is a perspective view of the test platform illustrated in FIG. 8.

The experimental platform used to assess wireless tissue palpation for a single degree of freedom is represented in FIG. 9. It included the WPD, the robotic manipulator, and the tissue sample under test.

Figure 10:
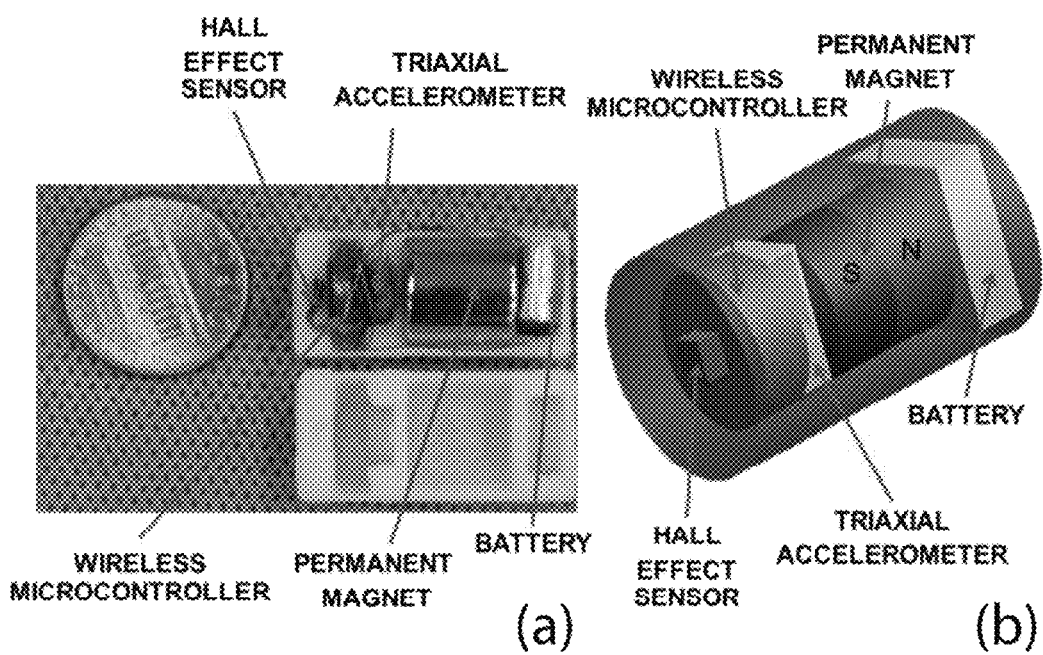
FIG. 10 is a schematic view and image of a device in the system illustrated in FIGS. 1-5.

The WPD embedded a permanent magnet, a sensing module, a wireless microcontroller, and a battery into a cylindrical shell (FIG. 10). We selected an off-the-shelf cylindrical NdFeB permanent magnet (K&J Magnetics, Inc., USA), 11 mm in diameter and 11 mm in height, with N52 axial magnetization (magnetic remanence of 1.48 T). The sensing module included a Hall effect sensor (CYP15A, ChenYang Technologies GmbH & Co. KG, Germany) to measure $B_Z$, and a triaxial accelerometer (LIS331AL, STMicroelectronics, Switzerland)—to verify that the WPD motion during indentation was limited to the Z direction.

An analog signal conditioning stage connected to the Hall effect sensor output allowed to cancel out the offset due to the onboard permanent magnet (i.e., 120 mT), to apply a low-pass filter (cut-off frequency of 30 Hz), and to amplify by 29 the magnetic field signal, resulting in a resolution of 0.32 mT and a sensing range of ±130 mT. An analog to digital converter (ADC) (ADS8320, Texas Instrument, USA) was used to acquire this voltage with a sampling rate of 1 kHz and a resolution of 16 bits. The result of the conversion was then transmitted through a serial synchronous interface to the wireless microcontroller (CC2530, Texas Instruments, USA). The signals generated by the accelerometer—that did not require a 16-bit resolution—were acquired directly by the microcontroller through its embedded 12-bit ADC at 100 Hz. Accuracy after digitalization resulted in 0.35 mT for the Hall effect sensor and 1.4 degrees for the accelerometer used as inclinometer. Real-time clock timestamps were associated with each single measurement to enable synchronization with signals acquired by the external platform. The data were transmitted over a 2.4 GHz carrier frequency to a receiving unit located in the same room and connected to a personal computer, where data were elaborated, displayed, and stored. The use of a 2.4 GHz carrier frequency was previously demonstrated to be effective in transmitting data through living tissues. The wireless microcontroller was integrated in a custom-made 9.8 mm diameter printed circuit board, together with radiofrequency components. A digital switch driven by the microcontroller was placed between the battery and the sensing circuitry, in order to save battery power when measurements are not required.

A 15 mAh, 3.7 V rechargeable LiPo battery (030815, Shenzhen Hondark Electronics Co., Ltd., China) was used as the power supply. The battery layout (8 mm×15 mm×3 mm) was reduced to fit the cylindrical shell. Considering that data acquisition and transmission requires an average of 33 mA, battery lifetime was almost 30 minutes. Operational lifetime can easily be extended to fit application requirements by maintaining the WPD in sleep mode (average current consumption of 1.5 µA) and waking up the system by remote triggering whenever a palpation task is going to be performed.

As represented in FIG. 10, all the components were integrated inside a cylindrical plastic shell fabricated by rapid prototyping (OBJECT 30, Object Geometries Ltd, USA). Due to its small size (12.7 mm in diameter and 27.5 mm in height), the WPD was introduced through a 12-mm surgical trocar (e.g., the 5-12 Vesaport Plus, Covidien, USA; has an inner diameter of 13 mm). An axial-symmetric design was pursued in order to keep the WPD center of mass along its main axis, thus guaranteeing a uniform pressure on the tissue. Considering vertical indentation, the WPD surface in contact with the tissue was 113 mm$^2$, while the total weight was 10 g. It is worth mentioning that a tether can be connected to the WPD, should the surgeon feel the need for a fast retrieval of the palpation device in case of failure.

Concerning the external part of the platform—represented in FIG. 9—an off-the-shelf cylindrical NdFeB permanent magnet (5 cm in diameter and 5 cm in height), with N52 axial magnetization (magnetic remanence of 1.48 T), was adopted. Considering an average thickness of the abdominal wall upon insufflation of 30 mm, this magnet was selected on the basis of numerical analysis to operate at a distance along Z ranging from 35 mm to 75 mm away from the WPD. In this region, the simulated values of the field gradient range from 3.75 T/m to 0.6 T/m, respectively. Considering the features of the magnet embedded in the WPD, the expected intermagnetic force spans from 4.7 N to 0.75 N.

Should the required working distance be increased due to specific patient constraints (e.g., larger body mass index), an external magnet with different features can be selected by running numerical simulations again.

The magnet was embedded in a plastic holder connected to a 6-axis load cell (MINI45, Ati Industrial Automation, Inc., USA), having a resolution of 65 mN for the Z component of the force. The magnet-load cell assembly was mounted at the end effector of a six degrees of freedom industrial robot (RV6SDL, Mitsubishi Corp., Japan), presenting a motion resolution of 10 µm along the Z direction. It is worth mentioning that the holder was designed to space the magnet enough from the load cell and the manipulator to prevent electromagnetic interferences. Data from the load cell were acquired by a dedicated acquisition board (NI-PCI 6224, National Instruments, USA) at a sampling frequency of 1 kHz, and merged with the manipulator position and the signals coming from the WPD.

A 34 mm thick tissue sample—silicone (M-F Liquid Plastic, MF Manufacturing, USA) in different stiffnesses or porcine liver, depending on the trial—was placed on a 2 mm thick rigid support, as represented in FIG. 9.

Finally, the algorithm described by Eq. 3 was implemented in Matlab (Mathworks, USA) upon experimental calibration.

In particular, the numerical function $\Phi^{-1}$ was evaluated by placing the WPD directly on the rigid support and by recording $B_Z(t)$ while moving the external magnet at a constant speed (i.e., 3.12 mm/s) from a starting position 75 mm away from the rigid support along the Z axis (i.e., $d_R$ varying from 0 mm to 75 mm, where for $d_R$=75 mm the top part of the holder was almost in contact with the lower side of the rigid support). This measurement was performed for five loading-unloading cycles, and the values were averaged. Given the exponential decay of the magnetic field with distance, a fifth-order polynomial function was used to fit $\Phi^{-1}$, thus obtaining:

$$d(t) = \Phi^{-1}[B_Z(t)] = \sum_{i=0}^{5} a_i \cdot B_Z(t)^i \qquad \text{Eq. 4}$$

with $a_0$=185.6 mm, $a_1$=−6.95·10$^3$ mm/T, $a_2$=1.57·10$^4$ mm/T$^2$, $a_3$=−2·10$^7$ mm/T$^3$, $a_4$=1.31·10$^7$ mm/T$^4$, $a_5$=−3.51·10$^7$ mm/T$^5$. The square of the correlation coefficient for the proposed fitting was $R^2$=0.99998.

Since the polynomial function is applied to a sensor reading affected by a given uncertainty $\Delta B_Z$, it is interesting to study the error propagation to the indentation depth $\delta$. Considering $\delta(t)$ as expressed in Eq. 3, we can write its absolute error as a function of $\Delta B_Z$ and $\Delta d_R$:

$$|\Delta \delta| = \left| \frac{\partial \Phi^{-1}[B_Z(t)]}{\partial B_Z(t)} \right| \cdot |B_Z| + |\Delta d_R| \qquad \text{Eq. 5}$$

Considering Eq. 3 and a negligible error in $d_R$—reasonable assumption given the high resolution of motion for the manipulator, we then have $$|\Delta \delta| = \left| \sum_{i=1}^{5} i \cdot a_i \cdot B_Z(t)^{i-1} \right| \cdot |\Delta B_Z| \qquad \text{Eq. 6}$$

This equation clearly shows how the accuracy of the proposed method depends upon the strength of the magnetic field at the WPD, which for the proposed platform, is a function of the distance between the external magnet and the WPD.

Experimental Results

Experimental validation of single degree of freedom wireless palpation consisted in three different trials. First, the effectiveness of the algorithm in reconstructing the indentation depth from magnetic field values was assessed. Then, three silicone tissue simulators, each with a different elastic modulus, were indented with the proposed approach, and the results compared with standard indentation. Finally, a spherical lump was embedded in a porcine liver and wireless palpation was used to identify differences in tissue stiffness.

A. Indentation Algorithm Assessment

An optical conoscopic holography sensor (Conoprobe, Optimet, USA) was adopted as reference measurement system. The conoprobe was mounted so to point the laser spot on the upper circular surface of the WPD, as in FIG. 9. The indentation test was performed on a squared silicone tissue sample (elastic modulus 6.45 kPa, thickness 34 mm, lateral side 74 mm) for $d_R$ varying at a constant speed (i.e., 3.12 mm/s) from 0 mm to 41 mm, where for $d_R$=41 mm the top part of the holder was almost in contact with the lower side of the rigid support. Five loading-unloading trials were carried out and error analysis was performed on the acquired data. Accelerometer output confirmed that WPD motion was always occurring along the Z direction.

Figure 11:
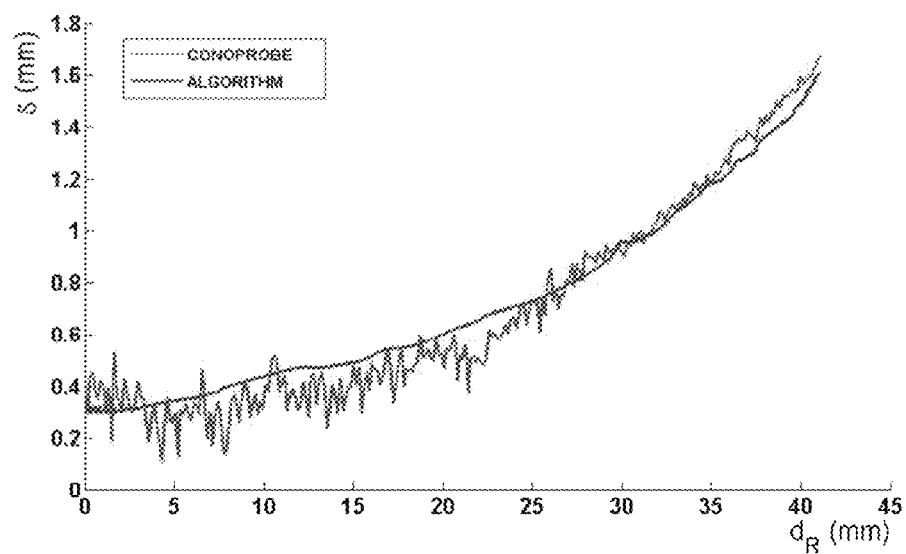
FIG. 11 is a graphical representation of tissue indentation depth plotted as a function of $d_R$ as reported in the study.

A typical loading plot for $\delta(t)$ acquired with both the reference system and the proposed approach is represented in FIG. 11 as a function of $d_R$. Considering the tissue sample thickness, the rigid support, and the recorded indentation depth, the distance d from the external magnet to the WPD varied from 75 mm to 35 mm during the trials.

Figure 12:
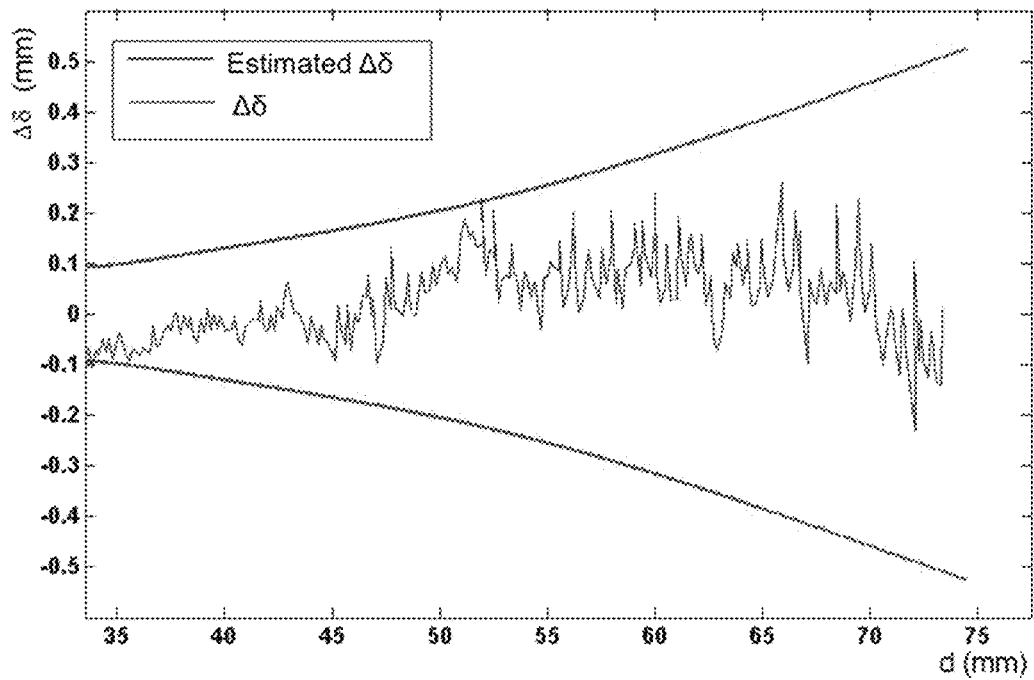
FIG. 12 is a graphical representation of tissue indentation depth error $\Delta\delta$ as a function of d as reported in the study.

Concerning the error, the Hall effect sensor measurements presented a standard deviation of ±0.3 mT. By using this value in Eq. 6 as $\Delta B_Z$, it is possible to plot an envelope of the expected standard deviation of the tissue indentation depth $\delta$ as a function of the distance d (FIG. 12). For all the acquired measurements, the difference between the conoprobe reading and the reconstructed $\delta$ always fell within the envelope. One example is given in FIG. 12. From the same plot it is possible to see that the standard deviation for $\delta$ is ±0.1 mm at 35 mm, while increases to ±0.5 mm at 75 mm.

B. In Vitro Trials

Figure 13:
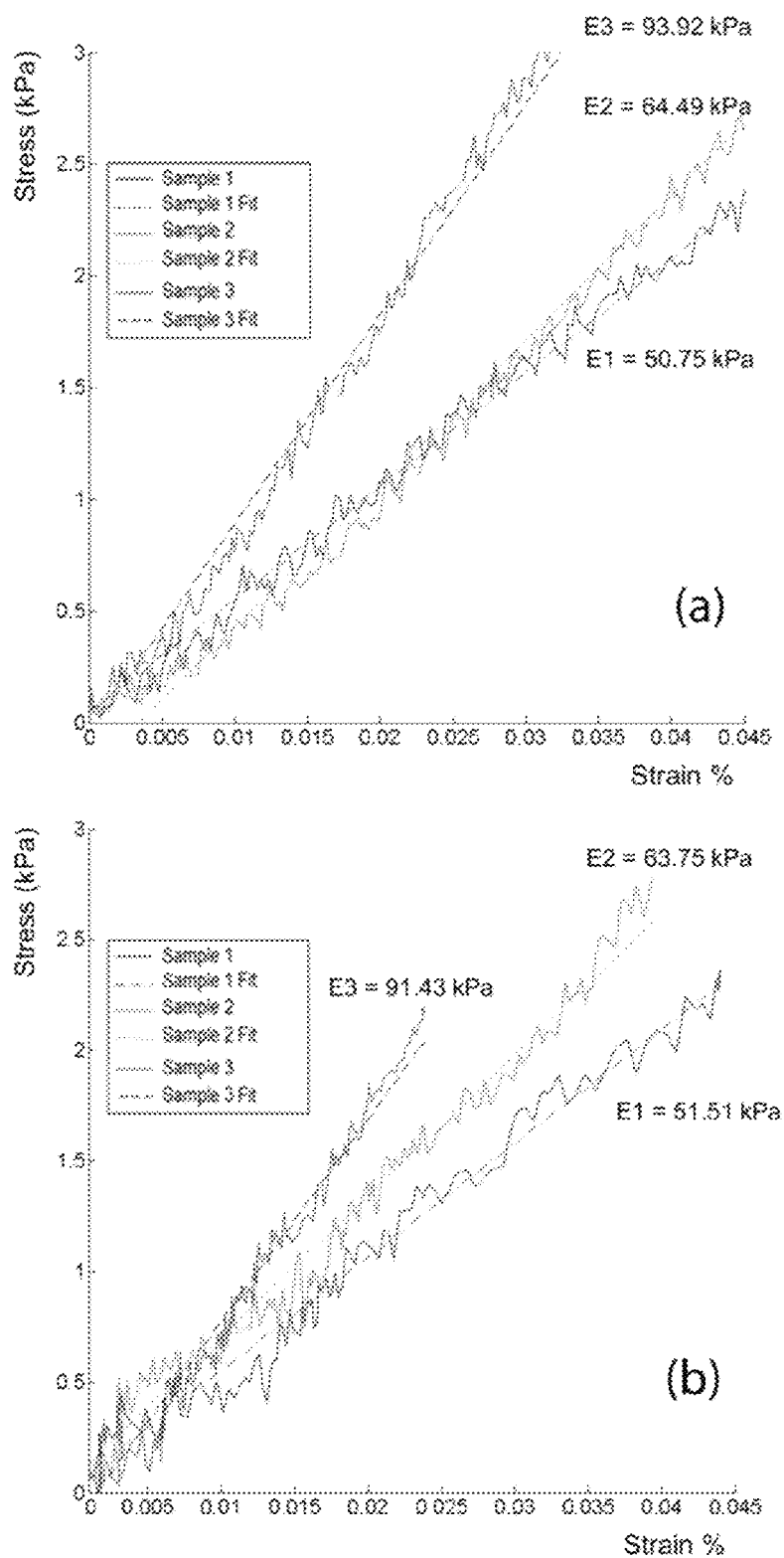
FIG. 13 is a graphical representation of experimental data as reported in the study.

In order to validate the effectiveness of wireless palpation to detect the elastic modulus of a tissue sample as a traditional indenter, three squared silicone tissue simulators (thickness 34 mm, lateral side 74 mm) were fabricated, each with a different proportion of hardener (i.e., 20%, 25%, and 30%), thus resulting in different elastic moduli E1, E2, and E3. A traditional vertical indenter was obtained by replacing the magnet holder with a cylindrical probe at the interface with the load cell. The probe was designed to have the same contact area as the WPD. The indenter probe was first driven to touch the surface of the tissue layer with a preload of 0.2 N. Five loading-unloading trials—reaching an indentation depth of 3 mm—were performed for each tissue sample at a constant speed of 3.12 mm/s. Stress-strain plots obtained from a single loading are represented in FIG. 13(*a*). Measured elastic moduli were E1=50.75 kPa, E2=64.49 kPa, and E3=93.92 kPa.

Wireless palpation was then performed on the same three samples. Five loading-unloading trials were performed by following the same protocol described for the assessment of the indentation algorithm described above. The results are reported in FIG. 13(*b*). Also in this case, accelerometer data confirmed that WPD motion was always occurring along the Z direction. Indentation force reached 2.2 N, while maximum indentation depth was 2.4 mm for the softer sample.

Considering all the performed trials, the average relative error for wireless palpation in measuring the elastic modulus was 1.49%, 1.14% and 2.65% for the tissue samples having E1, E2, and E3, respectively.

C. Ex Vivo Trials

A freshly excised porcine liver was used for the ex vivo trials. A 5 mm diameter sphere, fabricated by rapid prototyping in hard material, was embedded close to the tissue surface so as to simulate a hidden malignant liver tumor that is usually stiffer than the surrounding healthy tissue.

While most of our research work has focused either on providing force and tactile sensing at the end effector, or enabling haptic rendering at the user interface, the proposed approach tackles the physical connection between the two sides of the palpation instrument. The reported results lead to the conclusion that wireless vertical indentation is feasible in a laboratory setting, showing comparable results to traditional indentation techniques.

Surgeon Driven Wireless Palpation System

While the system 10 described above utilizes magnetic fields to indent the tissue, an alternative embodiment that includes a wireless device directly manipulated by the surgeon would be desirable. In this alternative embodiment, an intraoperative wireless palpation probe that can be deployed through a trocar incision and directly controlled by the surgeon to create a stiffness distribution map is described. The stiffness distribution map can then be used to localize tumor margins during the soft tissue surgery, thus improving intraoperative diagnostic and interventional decisions. The wireless operation prevents the need for a dedicated port and reduces the chance of instrument clashing in the operating field.

Figure 14:
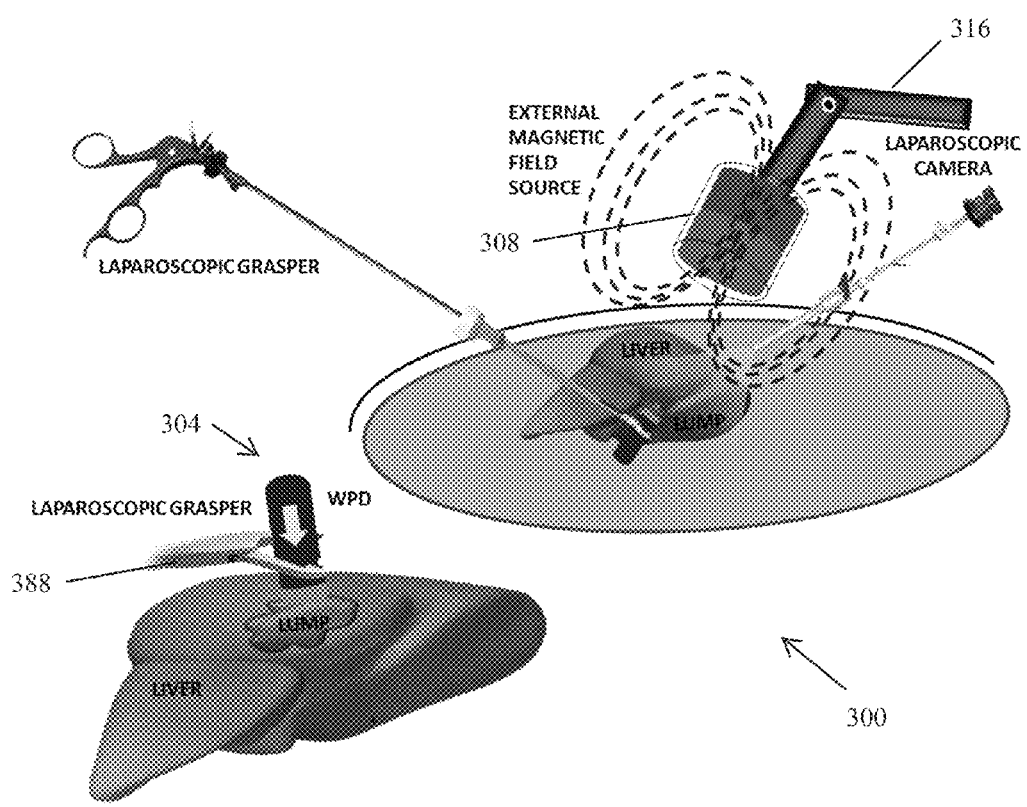
FIG. 14 illustrates a system for detecting tissue surface properties according to an embodiment of the present invention.

FIG. 14 illustrates a system 300 for detecting tissue surface properties according to an embodiment of the present invention. The system 300 includes a first device 304 (e.g., a wireless palpation probe ("WPP")) that can be inserted into the human body through a small incision for tissue palpation. Tissue palpation is essential to effectively explore nonvisible tissue and organ features to identify buried structures (e.g., nerves or blood vessels) that must be avoided during a surgical procedure, and to identify precise margins for curative tumor resections. Achieving negative surgical margins is particularly relevant during partial nephrectomies and hepatic surgeries in order to minimize accidental damage to healthy tissue and to prevent organ failure that would result in an urgent need for a transplant. Registration with preoperative imaging—a standard practice for image-guided surgery—is not a viable option for soft tissues. Therefore, surgeons currently rely on an intraoperative ultrasonography (IOUS) for the evaluation of vascular anatomy, identification of known and occult lesions, and operative planning Recent studies confirm the utility of IOUS also in robotic procedures, even if several open issues still remain unaddressed. In particular, IOUS can only provide a vertical slice of tissue density, while a stiffness distribution map would better serve the need of tumor margin identification.

For example, the system 300 can determine a tissue surface property related to local mechanical stiffness. For indentation depths that are less than 10% of the organ thickness, it is possible to assume that the tissue as linear elastic. A volumetric stiffness map can then be created by estimating the local tissue stiffness E(r) through the measurement of the indentation depth $\delta(r)$ and the tissue reaction pressure P(r) at different positions r on the organ surface $$E(r) \cong \frac{P(r)}{\delta(r)} \qquad \text{Eq. 7}$$

Figure 15:
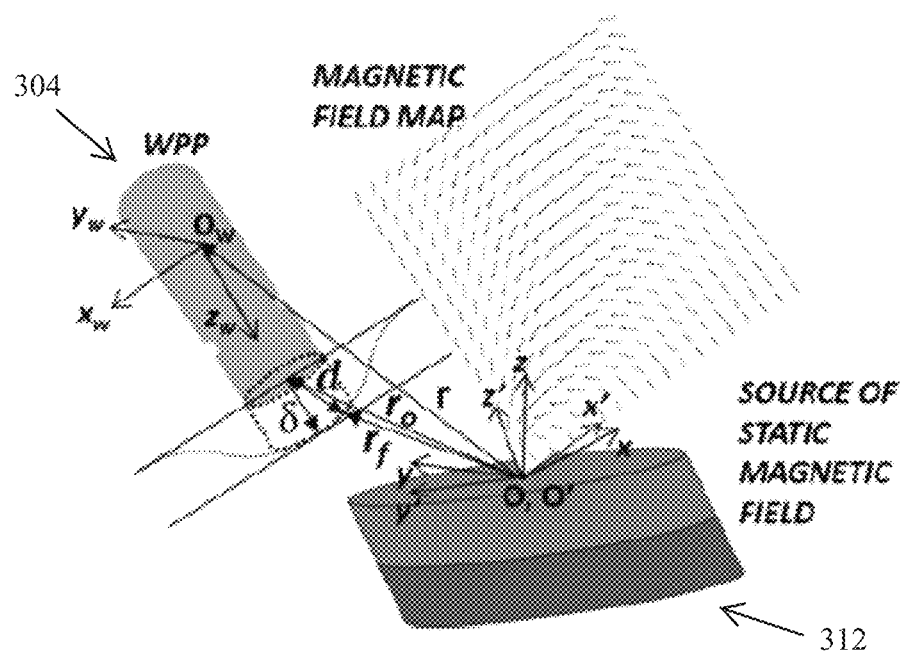
FIG. 15 schematically illustrates a device during indentation and the external source of magnetic field with a slice of the magnetic field map. Vectors $r_0$ and $r_f$ represent the device's position r at the beginning and at the end of the indentation. They are represented at the interface of the device and tissue, rather than at $O_w$, for a better understanding of their physical meaning

With reference to FIG. 15, we can define (x, y, z) as the global Cartesian coordinate system, (x', y', z') as the reference frame at the external source of the static magnetic field, and ($x_w$, $y_w$, $z_w$) as the coordinate system at the device 304.

The origin O of (x, y, z) is coincident with the origin O' of (x', y', z'), while $z_w$ is aligned with the main axis of the device 304. We can assume the position vector r to identify the origin of $(x_w, y_w, z_w)$—noted as $O_w$ with respect to the global coordinate system (x, y, z). When the device 304 is manipulated by the surgeon to palpate a tissue, its motion d is not constrained along $z_w$. Therefore, the following equation is used to estimate the indentation depth $\delta(r)$:

$$\delta(r) = d \cdot z_{w0} = (r_f - r_0) \cdot z_{w0} \qquad \text{Eq. (8)}$$

where $r_0$ and $r_f$ are the positions of the device 304 at the beginning and at the end of the indentation, respectively, while $z_{w0}$ is the unit vector along $z_w$ at the beginning of the indentation. In this approach, the beginning of the indentation is identified as the instant when the reading of the tissue reaction pressure P(r) becomes significant. The end of each indentation is identified as the instant when $\delta(r)$ reaches the maximum value.

The tissue reaction pressure is acquired by a barometric pressure sensor embedded in a silicone rubber at the probing surface of the device 304. A threshold value $P_{th}$, independent from r, is defined by calibration and takes into account both bias and noise of the pressure sensor. A single indentation starts as $P(r) > P_{th}$.

Real-time localization of the device 304 serves two purposes. First, the position where indentation is taking place is recorded in three degrees of freedom (DoF) in order to reconstruct the stiffness map. In this case, we assume the position r of each indentation to be coincident with the position of the device 304 as the indentation begins (i.e., $r_0$). A second goal for tracking the device 304 is to derive $\delta(r)$ as in Eq. 8. In this case, real-time estimation of r and rotations of the device 304 around x and y are required. Therefore, the position and orientation in five DoF of the device 304 must be available in real time. This is achieved by an on-board localization module, working in synergy with an external source of the static magnetic field as represented in FIG. 14. The on-board module comprises three orthogonally mounted magnetic field sensors and an inertial sensor, such as a triaxial accelerometer (technical details are discussed below). The accelerometer—used here as an inclinometer—provides the rotations of the device 304 around x and y. The position vector r of the device 304 is derived from the magnetic field sensor readings. In particular, the magnetic field vector $B_w$ is measured at the device 304 and rotated according to $$B = R'^T R^w R' B_w \qquad \text{Eq. (9)}$$

where $R^w$ is the rotational matrix of the reference frame of device 304 with respect to the global Cartesian coordinate system, while R' is the rotational matrix of the reference frame at the external source of the static magnetic field with respect to the global Cartesian coordinate system. The matrix $R^w$ is obtained in real time from the readings acquired by the inclinometer integrated in the device 304, while R' is derived from the data acquired by an inclinometer mounted on the external source of the static magnetic field. Then, a search within a precalculated bidimensional magnetic field map is performed to find the position r of the device 304 that would match with the actual magnetic field vector B. The magnetic map associates each point r within the workspace—expressed in cylindrical coordinates $(r_p, r_z)$—to the related magnetic field intensity B—also expressed in cylindrical coordinates $(B_p, B_z)$—with a spatial resolution of 0.2 mm. The third cylindrical coordinate $r_\theta$ can be calculated from the values of $B_x$ and $B_y$ by applying the following equation:

$$r_\theta = \arctan\left(\frac{B_y}{B_x}\right) \qquad \text{Eq. 10}$$

The effective localization workspace is a cylinder with a diameter of 35 cm and a length of 35 cm, centered on the static magnetic field source. The 5-DoF device 304 coordinates derived by the algorithm are referenced to a Cartesian frame at the center of the workspace.

Figure 16:
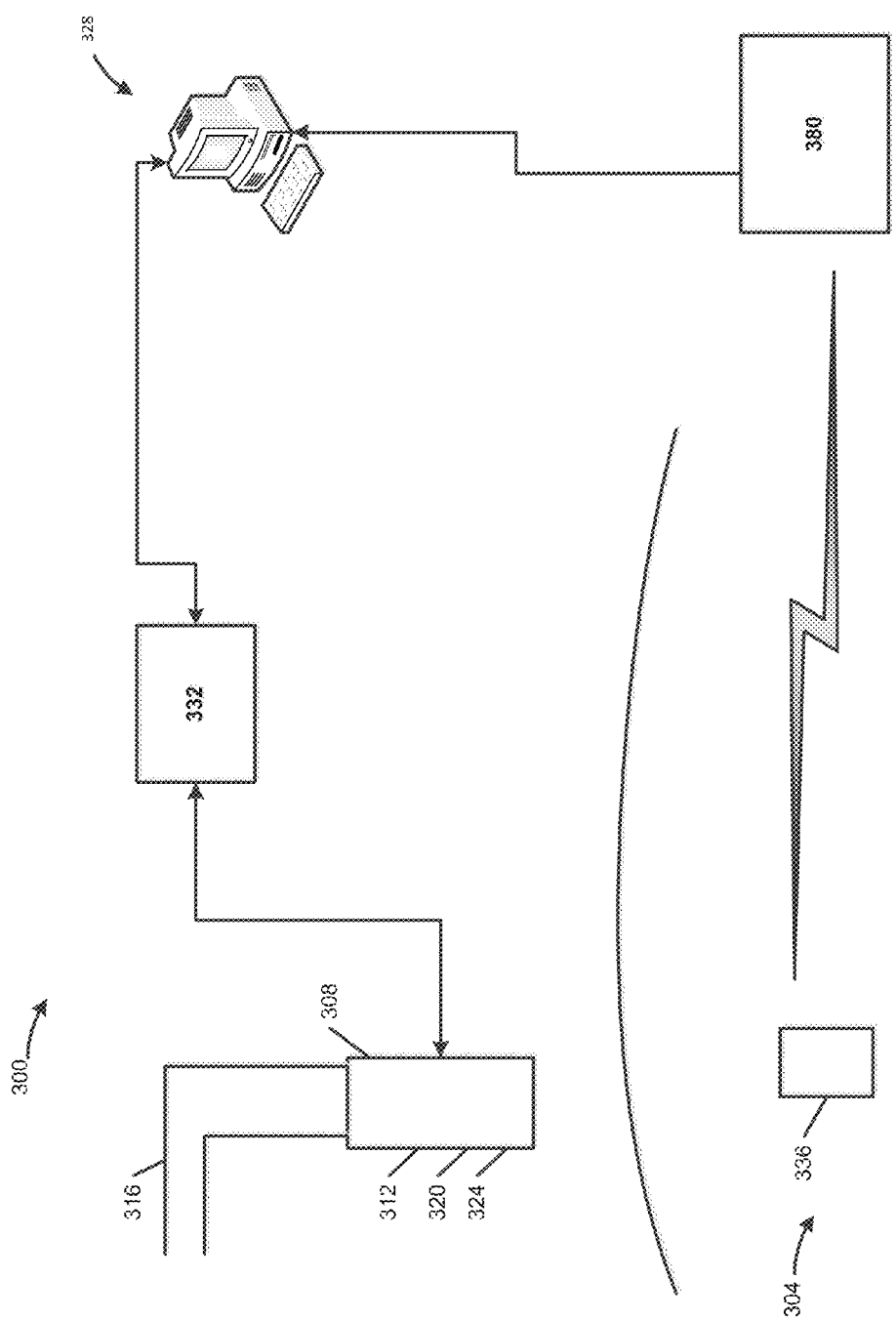
FIG. 16 is a schematic view of the system for detecting tissue surface properties illustrated in FIG. 14.

With reference to FIG. 16, the system 300 comprises a first housing 308 configured to support a static magnetic field source 312 (e.g., permanent magnet or electromagnet) for tracking the device 304. The first housing 308 is mounted to an arm 316 that is positionable outside the patient's body. In one construction, the arm 316 comprises an articulated three-DoF friction clutch arm (Dectron, Roswell, Ga., USA). The static magnetic field source 312 comprises a permanent magnet 320 (e.g., NdFeB cylindrical permanent magnet) to generate a magnetic field. In one construction, the permanent magnet 320 comprises N52 axial magnetization, magnetic remanence of 1.48 T, is 50 mm in diameter and 50 mm in height, and has a mass of 772 g. These features allow for a localization workspace that extends 15 cm away from each side of the magnet.

The first housing 308 also supports an inertial sensor 324, such as an accelerometer or gyroscope. In one construction, the inertial sensor 324 comprises a triaxial accelerometer 324 (LIS331AL, STMicroelectronics, Geneva, Switzerland), which is mounted on the magnet 320 to measure its inclination and derive its rotation with respect to the global reference frame (x, y, z). The inertial sensor data is transmitted (via hardwire connection or wirelessly) to a computer 328. The computer 328 can include a computer program 332 configured to receive the signals from the inertial sensor 324. The computer program 332 when operated by a computer or processor 328 can process or compute a relevant output for presentation on a display or computer monitor. The output can represent position and orientation of the device 304 relative to a reference frame.

Figure 17:
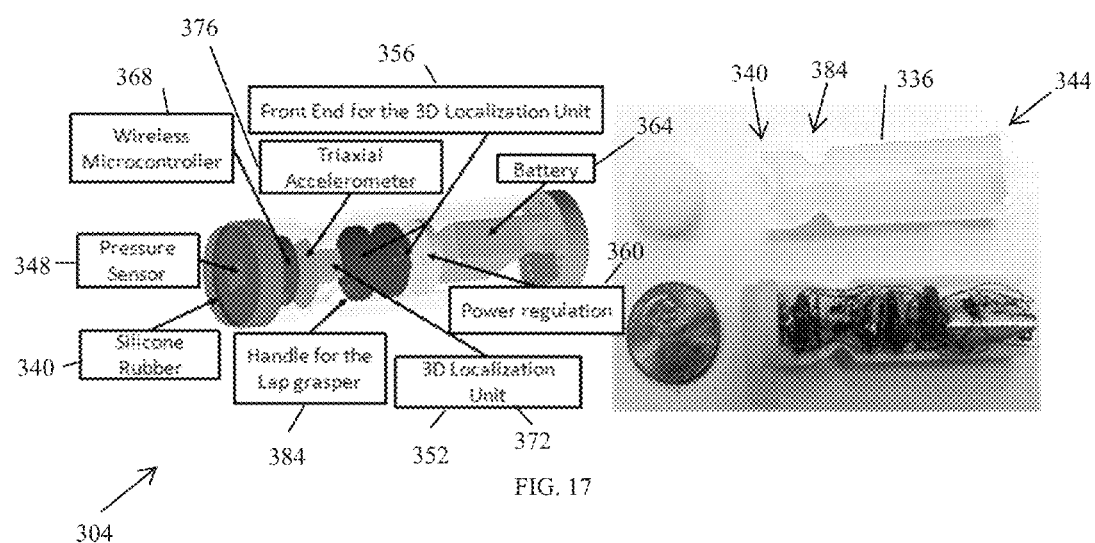
FIG. 17 is a schematic view of a device in the system illustrated in FIG. 14.

With reference to FIGS. 16-17, the device 304 includes a second housing 336 configured for positioning inside a patient's body near a target location. The second housing 336 is enclosed and is generally cylindrical-shaped and includes a first end 340 and a second end 344. In one construction, the second housing 336 is about 15 mm in diameter and about 60 mm long, and the device 304 weighs about 9.5 g. The second housing 336 may include a layer of paraffin film (Parafilm, Sigma Aldrich, St. Louis, Mo., USA) wrapped around the housing 336 to make the device 304 waterproof. An additional layer of film may be applied to a grasping site (discussed below) to enable a secure grip.

Figure 18:
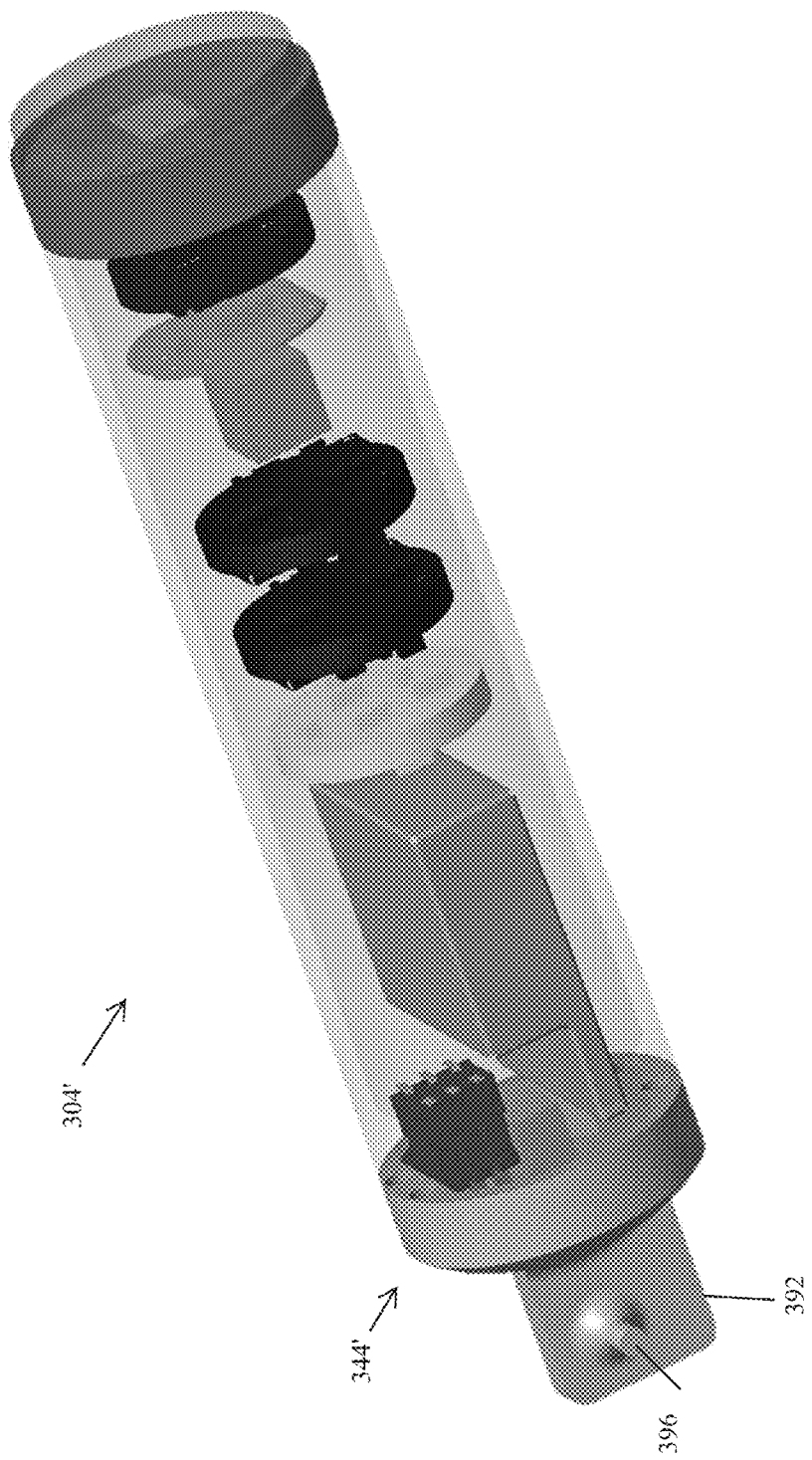
FIG. 18 is a schematic view of an alternative device in the system illustrated in FIG. 14.

With further reference to FIG. 17, the second housing 336 includes a grasping site 384. As illustrated in FIG. 17, the grasping site 384 comprises a reduced diameter area positioned closer to the first end 340 than to the second end 344 and provides an area for a grasper 388, such as a laparoscopic grasper, to grip the device 304. A surgeon can then manipulate the grasper 388 to move the device 304 around and make contact with the target location (e.g., applying an indentation force to the target location or region of interest). FIG. 18 illustrates an alternate construction of the device 304, referred to herein as device 304'. The device 304', while including substantially the same components (and not further discussed) as in the device 304, includes a grasping site 384 that comprises an extension 392 from the second end 344'. The extension 392 includes a post 396 extending transversely therefrom on both sides of the post 396. A surgeon can utilize a grasper 388 to grip the post 396 to move the device 304' around and make contact with the target location. The grasping site 384 may comprise other suitable mechanisms that allow a tool to grip the second housing 336. In addition, the grasping site 384 may be located in the middle of the second housing or closer to the second end 344 than the first end 340.

The second housing 336 supports a pressure sensor 348, a localization module 352 with a signal conditioning stage 356, a power regulation module 360, a power source 364, and a processor or microcontroller 368. The pressure sensor 348 is positioned adjacent the first end 340, and in one construction, comprises a barometric pressure sensor (MPL115A1, Freescale Semiconductors, Austin, Tex., USA) embedded in a 2.2 mm thick silicone rubber layer 340 (VytaFlex 20, Smoth On, Easton, Pa., USA). The barometric pressure sensor has a sensitivity of 0.5 kPa and a sensing range of 65 kPa for the atmospheric pressure.

The localization module 352 includes a plurality of magnetic field sensors 372 and an inertial sensor 376 (e.g., accelerometer or gyroscope). In one construction, the localization module 352 comprises three Hall effect sensors (CYP15A, ChenYang Technologies GmbH & Co. KG, Finsing, Germany) and a 16-bit triaxial accelerometer with serial peripheral interface (SPI) (LIS331AL, STMicroelectronics, Geneva, Switzerland). The Hall effect sensors are mounted on three surfaces orthogonal to each other, such as, for example on three orthogonal sides of a cubic structure as illustrated in FIG. 17. In other constructions, more than three magnetic field sensors (e.g., Hall effect sensors) can be utilized. The analog outputs of the Hall effect sensors are acquired by the signal conditioning stage 356, which comprises amplifiers, filters, and A/D converters. In one construction, the signal conditioning stage 356 comprises three instrumentation amplifiers (AD623, Analog Devices, Norwood, Mass., USA) with a unity gain, three low-pass filters ($F_c$=30 Hz), and three 16-bit analog to digital converters (ADS8320, Texas Instruments, Dallas, Tex., USA) with SPI interface. The digitalized magnetic field signal has a sensitivity of 0.6 mT.

The power regulation module 360 includes a voltage regulator and an operational amplifier. In one construction, the power regulation module 360 comprises a low-dropout voltage regulator (TPS73xx, Texas Instruments, Dallas, Tex., USA) and an operational amplifier (ADS8617, Analog Devices, Norwood, Mass., USA) used as a voltage divider to provide the proper power supply to the signal conditioning stage 356 and to monitor the battery level. The power source 364, comprises, in one construction, a 50 mAh, 3.7 V rechargeable LiPo battery (Shenzhen Hondark Electronics, Co., Ltd., Shenzhen, China, 12 mm×15 mm×3 mm in size). In another construction, the second housing 336 is about 9.9 mm in diameter with the signal conditioning stage 356, the triaxial accelerometer 376, the power regulation unit 360, and the wireless microcontroller 368 mounted on separate printed circuit boards (PCB).

The data from the pressure sensor 348 and the localization module 352 are acquired by the processor 368, which in one construction comprises a wireless microcontroller (CC2530, Texas Instruments, Dallas, Tex., USA) through the SPI interface at a clock frequency of 1 Mbit/s. Each dataset is then bounded into a 28-byte payload together with a progressive package indicator, a time stamp, the battery level, and two synchronization start and stop bytes. This payload is transmitted by the processor 368 to an external transceiver 380 over a 2.4-GHz carrier frequency. The external transceiver 380 comprises a mirror wireless microcontroller (CC2530, Texas Instruments, Dallas, Tex., USA) connected to the computer 328. The transceiver 380 may be connected to the computer 328 via a USB port through a dedicated module (UM232R, FTDI, Glasgow, U.K.).

In one construction, it takes about 3.7 ms to acquire a single dataset from all of the sensors with the wireless data throughput running at 44.8 kbit/s, resulting in a refresh time of about 5 ms and a sampling rate of 200 Hz. The overhead allows correct handling of the synchronization with the external transceiver 380.

The communication protocol provides robust operation, real time data acquisition, and low power consumption. A sleep timer is used to wake up the device 304 from a low-power mode every 15 s. When active, the device 304 tries to establish a wireless communication with the external transceiver 380. If this attempt fails, the device 304 returns to sleep mode to save power. Once the wireless link is established, the device 304 acquires a full dataset of sensor readings, transmits it to the external transceiver 380, and waits for an acknowledgement. If the acknowledgment is received, the device 304 continues to acquire and send data. Otherwise, the device 304 retries to transmit the same package. This attempt is repeated for two times, then, the firmware forces the device 304 to get a new dataset and updates the payload. In case of loss of the synchronization, the device 304 auto resets itself ready for a new acquisition. This protocol allows for a fail safe operation and prevents the need for a hard reset of the device that would not be possible during surgery.

The data received by the external transceiver 380 is transmitted to the computer 328 together with the received signal strength indicator (RSSI). The RSSI quantifies the quality of the wireless link. In case of a low RSSI, the user is warned to modify the position of the external transceiver 380 to improve the wireless coupling.

A multithread C++ application running on the computer 328 unbounds the data and shares them with a parallel application developed in MATLAB (Mathworks, Natick, Mass., USA) via TCP-IP communication. Refresh rate for displayed data runs at 30 Hz.

Figure 25:
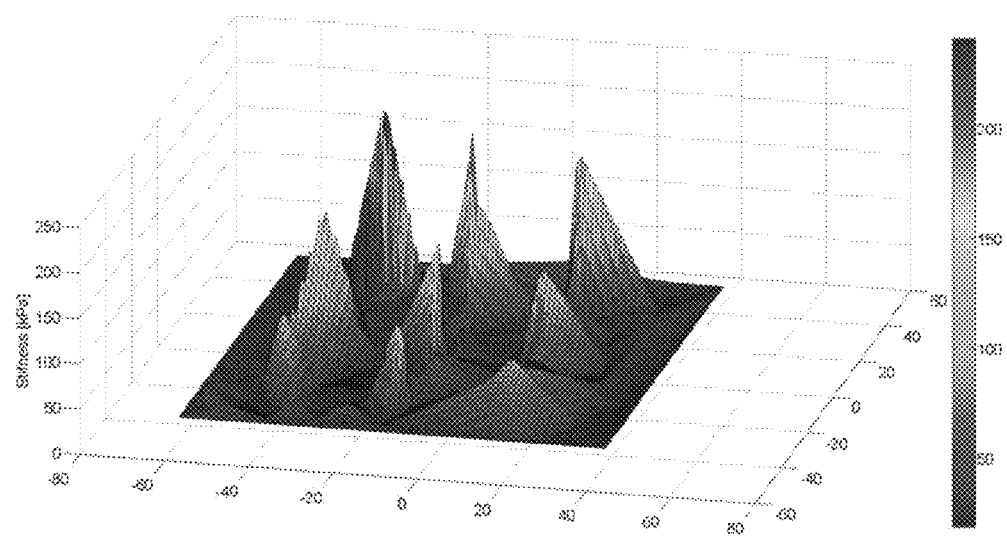
FIG. 25 is a graphical representation of a volumetric tissue stiffness map.

The user interface is conceived to work in two different modalities: 1) creation of the volumetric stiffness map (see FIG. 25, for example) and 2) display of position of the device 304 on the volumetric stiffness map. In the first modality, the surgeon grasps the device 304 and creates the map by palpating the region of interest. In this case, the user interface displays in real time the x, y, z coordinates of the device 304, a plot of the indentation pressure, and the numeric value of the indentation depth in case the indentation pressure has exceeded $P_{th}$. Visual indicators are provided to warn the user if the device 304 is outside the localization workspace. Once the region of interest has been palpated with the desired spatial resolution, a command is provided by the user through the keyboard to create the volumetric stiffness map. Once the map is available, the user interface switches to the second modality, overlaying the real-time position of the device 304 in a 3-D space centered on the map. Under the assumption that the region palpated does not undergo substantial movements, the surgeon can manipulate the device 304 as a cursor to identify the margins of a stiffer region buried underneath the tissue.

Experimental Results

Before assessing the overall functionality of the proposed device, the single components were tested and characterized on the benchtop. In particular, the first step was to verify the localization unit algorithm to evaluate the workspace of the device 304, localization error, and any influence of surgical tool in the localization unit performance. Then, a load cell was adopted to calibrate the pressure sensor response. Finally, the electronic performance of the device 304 was tested on the bench to assess the battery lifetime and the wireless link reliability.

1) Localization: The device 304 was mounted on the end effector of a six DoF industrial robot (RV6SDL, Mitsubishi Corp., Tokyo, Japan) which was used as a reference position system given its encoder feedback. Assuming the (x, y, z) global reference system centered on the external magnet and having z aligned with the main axis of the magnet, we characterized the localization on a grid of 3 by 3 points equally spaced by 50 mm along x- and y-directions at three different z coordinates (i.e., 80, 110, and 140 mm). For each position, localization data were acquired from the robot encoders and the algorithm of the device 304. Onboard localization was repeated for each point with a disposable laparoscopic grasper (EndoGrasp 5 mm, Covidien, Mansfield, Mass., USA) closing its jaws at the grasping site. Then, the indentation depth error was estimated at each point of the grid by moving the robot end effector 3 mm along z in open air, thus emulating palpation. The average absolute errors were equal to 4.7 mm (±4.5 mm) for x, 4.1 mm (±5.8 mm) for y, and 4.5 mm (±2.2 mm) for z. The laparoscopic grasper increased the localization error to 9.8 mm (±5.1 mm) for x, 11.3 mm (±6.6 mm) for y, and 10.6 mm (±4.6 mm) for z. However, we observed that the contribution of the laparoscopic grasper does not vary substantially within the workspace, thus, it can be assumed as a constant offset that factors out when reconstructing the stiffness map. The indentation depth average absolute error resulted in 0.68 mm (±0.44 mm).

Figure 19:
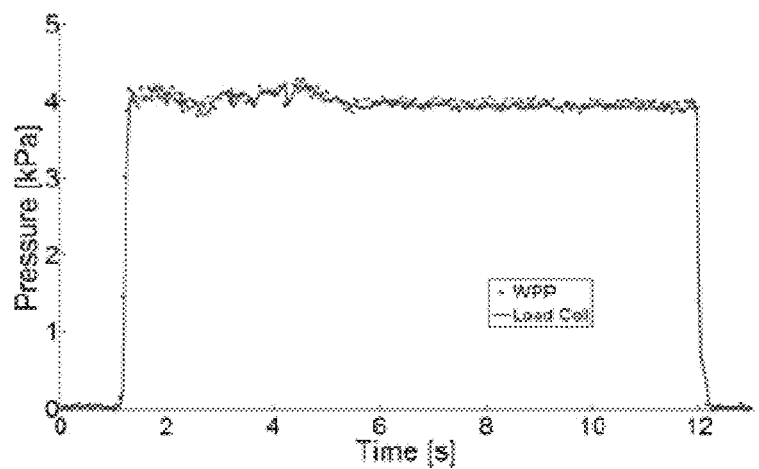
FIG. 19 is a graphical representation of the step response of the device pushing against a reference load cell.

2) Pressure Sensing Head: To calibrate and characterize the pressure sensing head response, a 6-DoF load cell (NANO17, ATI Industrial Automation, Apex, N.C., USA, resolution 1/160 N) was adopted as the force reference system. The device 304 was mounted as in the previous experiment, while the load cell was fixed on the benchtop. A 1-mm step motion pushing the device 304 against the load cell was imposed. Speed of motion was 65 mm/s. After about 9 s, the same step was imposed in the opposite direction, releasing the load. From the experimental results—represented in FIG. 19—we can conclude that the silicone layer embedding the barometric pressure sensor 348 does not introduce any relevant delay in the sensor response. An additional set of trials was performed by pushing the device 304 against the load cell at a lower speed (i.e., 3.12 mm/s), until the saturation of the barometric pressure sensor 348 occurred. This test was repeated five times. The pressure sensing head showed a sensitivity of Ps=34 Pa (i.e., considering the probing area, this is equivalent to 5 g or 0.049 N), while saturation occurred at PSAT=5 kPa (i.e., considering the probing area, this is equivalent to 730 g or 7.16 N). In light of a recent study (M. T. Perri et al.,"New tactile sensing system for minimally invasive surgical tumour localization," Int. J. Med. Robot. Comput. Assist. Surg., vol. 6, no. 2, pp. 211-220, 2010) that reports tissue damage to the liver for a force exceeding 6 N—exerted by a probing area of the same size of the device 304—we can conclude that the pressure sensing range is adequate for this exploratory investigation. The threshold value $P_{th}$ was therefore assumed as $P_{th}=P_{bias}+2P_s$, where $P_{bias}$ is the output value for the sensor when unloaded. This value for $P_{th}$ allowed us to reliably identify the start of an indentation.

3) Electronics: As regards power consumption, a single 5-ms loop of data acquisition and wireless transmission drains an average of 33.3 mA with a peak of 41.6 mA. This translates in a battery lifetime of about 90 min when the device 304 is in the active mode. The average current consumption drops down to 3 mA when the device 304 is in low-power mode.

The data synchronization between the device 304 and the external transceiver 380 was tested in open air to estimate the robustness of the protocol. The firmware was run for 36 consecutive hours without failures and was then stopped. The results included a package loss below 2% and an average RSSI of −13.5 dBm at a distance of 2 m between the device 304 and the external transceiver 380. Complete loss of communication occurs as the RSSI drops below −88 dBm.

Experimental validation of the proposed platform consisted in two different trials. First, the effectiveness of the probe in identifying the local stiffness of a tissue simulator was assessed. Then, in vivo trials were aimed to identify agar-gel lumps injected into a porcine liver and to assess the device usability within the frame of an MIS procedure.

A. Assessment of Local Stiffness Identification

Figure 20:
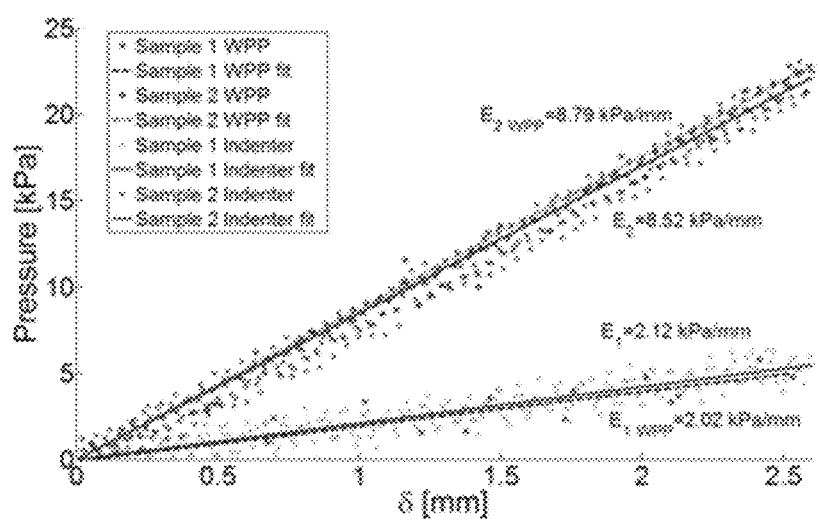
FIG. 20 is a graphical representation of experimental data acquired by standard and wireless indentation for two different silicone samples. For this trial, relative errors in local stiffness identification were equal to 4.72% for sample 1 and 3.17% for sample 2.

To estimate the ability of the device 304 in detecting different local stiffnesses, two different synthetic tissue samples were fabricated combining two different ratios of liquid plastic and hardener (PVC Regular Liquid Plastic—Hardener, MF Manufacturing, Fort Worth, Tex., USA—Sample 1: 1 to 10 ratio, resulting in an elastic modulus of 220 kPa; Sample 2: 1 to 2 ratio, resulting in an elastic module of 45 kPa). The samples were 30 mm thick with a lateral side of 75 mm. A traditional indenter was obtained mounting a 6-DoF load cell (MINI 45, ATI Industrial Automation, Apex, N.C., USA, resolution 1/16 N) at the end effector of the robotic manipulator used previously. A cylindrical probe with the same contact surface as the device 304 was mounted on the distal side of the load cell to indent the sample. Then, the cylindrical probe was replaced with the device 304 and the indentation was repeated acquiring both the indentation pressure and depth from the wireless device. Five loading-unloading trials reaching an indentation depth of 2.6 mm were performed for each tissue sample and each method at a constant speed of 0.75 mm/s. The local stiffnesses measured with the traditional indenter were equal to $E_1=2.12$ kPa/mm, $E_2=8.52$ kPa/mm, while the results obtained with the device 304 were $E_{1wpp}=2.02$ kPa/mm, $E_{2wpp}=8.79$ kPa/mm. Experimental plots obtained from a single loading are represented in FIG. 20. Overall, the device 304 was effective in detecting the local stiffness of different samples with an average relative error equal to 4.7% for sample 1 and 3% for sample 2.

B. In Vivo Validation

The feasibility of wireless tissue palpation was then assessed in vivo on an anesthetized porcine model. The primary measure of interest was to acquire a volumetric stiffness map of a segment of the liver where agar-gel was injected to simulate a hepatic tumor. The map acquired in vivo by wireless palpation was then compared with a stiffness map obtained post-mortem within 12 h after the procedure using a standard uniaxial material tester. Secondary measures of interest were the time to scan a liver segment by wireless palpation, device 304 usability, instrument clashing, and operator workload. Reliability of the wireless link was also assessed.

Figure 21:
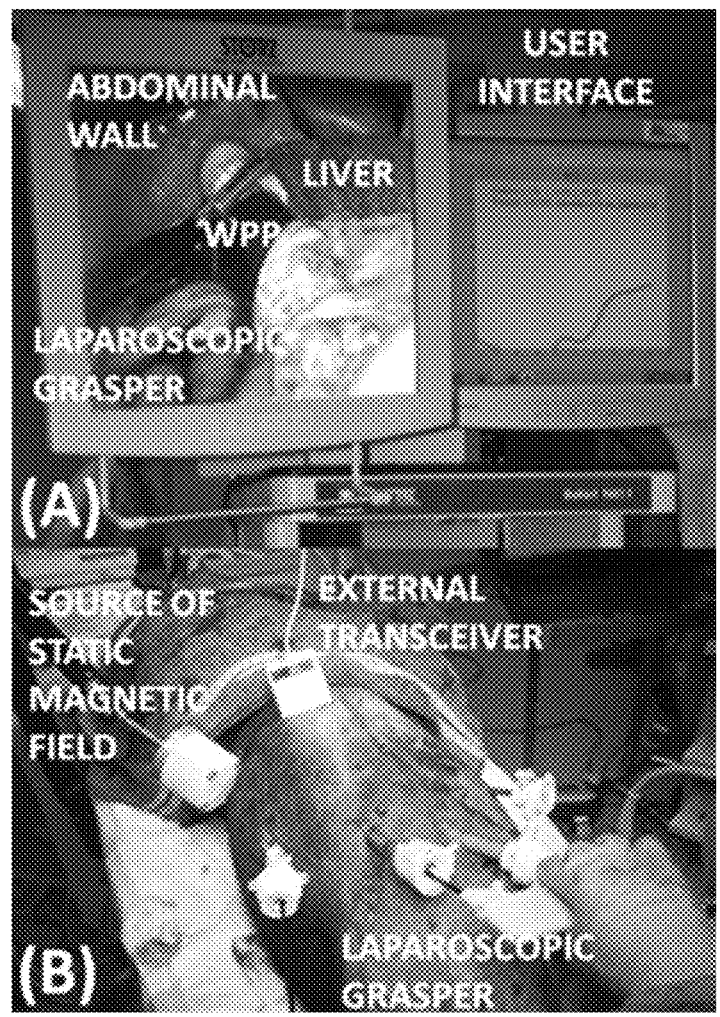
FIG. 21 is a picture of the surgical setup during the in vivo trial; (a) is a snapshot of the laparoscopic camera view and the user interface during the creation of the volumetric stiffness map; (b) is a picture of the surgical field.
Figure 22:
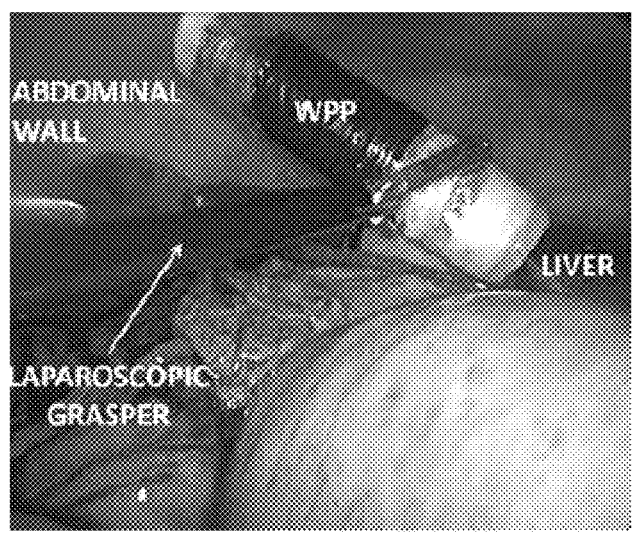
FIG. 22 is a laparoscopic view of the device operated by the surgeon through a laparoscopic grasper during in vivo trials.

The porcine surgery was performed at the University of Colorado Anschutz Medical Campus under IACUC protocol 87912(04)1D. A 57-kg female standard pig was used for this study. After intravenous sedation, a laparotomy was performed to access the liver. Six cc of Sigma Gelrite Gellan Gum (agar) was prepared in a 30:1 ratio of water to agar by weight, boiled, and injected into the right lateral segment of the liver, to approximately the midthickness of the organ. The midline incision was then sutured, and minimally invasive access was gained by one 5-mm (SVersaport Plus, Covidien, Norwalk, Conn., USA) and three 12-mm trocars (5-12Versaport Plus, Covidien, Norwalk, Conn., USA). The device 304 was introduced in the abdominal cavity through one of the 12-mm trocar incisions before the placement of the port. The external source of the magnetic field 312 and the external transceiver 380 were placed in the close vicinities of the right side of the animal, as represented in FIG. 21(*b*). The surgeon used a standard laparoscopic grasper to operate the device 304 under endoscopic guidance (see FIG. 22). A lateral screen showed in real-time the position of the device 304 in three DoF, indentation pressure, and indentation depth [see FIG. 21(*a*)].

Figure 23:
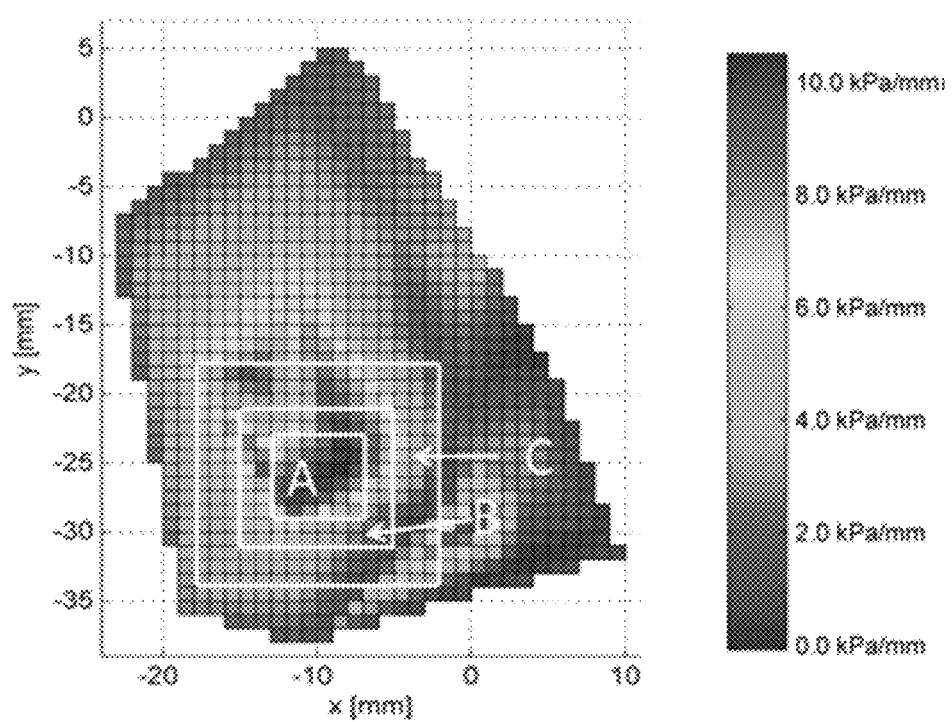
FIG. 23 is a local stiffness map acquired in vivo for a 6 cc agar-gel lump injected into the porcine liver. Since the surface of the porcine liver was almost flat in the palpated region, a bidimensional projection of the map is shown. The local stiffness values inside areas A, B, and C were compared with the ex vivo map represented in FIG. 24.

Once the right segment of the liver was identified, the surgeon palpated the organ in different positions, always targeting at least 3 mm as the indentation depth. To prevent localization artifacts, the surgeon verified that the liver was not moving during palpation and that adequate support was provided by the rib cage and the surrounding organs. Tissue stiffness was acquired on a total of 30 different points on the liver surface. This required about 5 min. The local stiffness map, represented in FIG. 23, was then generated by the algorithm and displayed on the lateral screen, overlaying the current position of the device 304.

Figure 24:
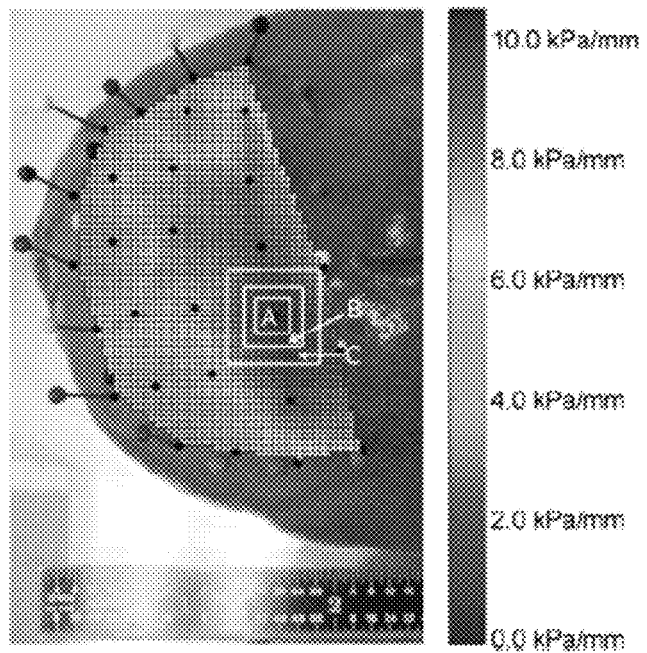
FIG. 24 is a stiffness map obtained with a standard uniaxial MTS, overlayed on the right lateral segment of the explanted porcine liver. The local stiffness values inside areas A, B, and C were compared with the in vivo map represented in FIG. 23.

Immediately after euthanization, the liver was harvested from the animal for ex vivo palpation tests using a standard uniaxial material testing system (MTS) (Insight 2 Electromechanical Testing System, MTS System Corporation, Eden Prairie, Minn., USA) to create a comparable stiffness map. The liver was placed in 0.9% phosphate buffered saline (PBS) solution immediately after excision and refrigerated until the ex vivo tests were performed. The liver was warmed to room temperature prior to testing. The organ was placed on a platform, marked with 28 pins and photographed from the top (see FIG. 24). The liver was indented with a cylindrical indenter probe (2-mm diameter) beside each pin location—to avoid palpating tissue that had been pricked by the pin. The test was performed following a standard tissue compressive property measurement method (X. Wang et al. "Quantitative comparison of soft tissue compressive viscoelastic model accuracy," *J. Mech. Behav. Biomed. Mater.*, vol. 20, pp. 126-136, 2013). The tissue was hydrated throughout the tests by spraying PBS on the surface prior to each indentation. The testing room conditions were 23.5° C. and 22% relative humidity. A 2-N load cell (PN LCCA-118-75, MTS System Corporation, Eden Prairie, Minn., USA) with 1-mN resolution was used to measure the load exerted on the tissue by the indenter during each indentation. The probe was programmed to approach the surface of the tissue at a low speed (0.1 mm/s) until a force threshold (2 mN) was reached. At that point, the probe advanced into the tissue at a rate of 1 mm/s to a depth of 3 mm to simulate the in vivo experiment. The force and indentation depth (10 μm resolution) data were collected at 100 Hz and analyzed with a customized program developed in MATLAB. Following testing, the tissue was resected to verify that the agar did not dilute in the liver.

The force data were divided by the surface area of the cylindrical probe tip to obtain pressure. The local stiffness at each point was determined by computing the slope of a linear regression of the first 0.75 mm of the pressure-displacement curve. The force at depths larger than 0.75 mm was found to be too high due to the rigid platform that the liver was resting on and the relatively small liver thickness. This was not an issue in vivo as the liver was pressed against other organs or the rib cage. The stiffness values were assigned to pin locations and overlaid on the photograph of the liver to produce the stiffness map shown in FIG. 24.

The two local stiffness maps were then compared with MATLAB (grid area is equal to 1 mm2 for both the maps). In particular, the maximum measured stiffness resulted in 10.0 kPa/mm with the MTS machine versus 10.8 kPa/mm with the device 304, corresponding to an 8% relative error. Then, the average pseudo stiffness of the three different areas A (36 mm$^2$), B (64 mm$^2$), and C (156 mm$^2$) centered on the maximum point were compared. Area A is a square sided 6 mm, area B is the frame with outer dimension 10 mm, and inner dimension 6 mm, while the area C is the frame with outer dimension 16 mm and inner dimension 10 mm. The three areas are shown in both the FIGS. 23 and 24. The average stiffness was equal to $E_{AMTS}$=9.64 kPa/mm and $E_{AWPP}$=8.87 kPa/mm (average relative error 7.96%), $E_{BMTS}$=9.20 kPa/mm and $E_{BWPP}$=6.58 kPa/mm (average relative error 28.5%) and $E_{CMTS}$=8.64 kPa/mm and $E_{CWPP}$=4.82 kPa/mm (average relative error 44.2%). The tissue stiffness slightly increased after euthanization and throughout the MTS testing due to the preservation and dehydration. However, the stiffness at the injection site remained constant to the in vivo conditions because the gel properties did not vary after explantation. This can help explain why the relative error increases with the distance from the maximum point which is nearby the injection site.

As concerns the qualitative measures of interest, no instrument clashing was reported. However, the length of the device 304 limited the range of motion whenever the target of palpation was too close to the ribcage. The operator workload was minimal since the surgeon was able to use a standard laparoscopic instrument to operate the device 304. Relevant learning occurred just at the beginning of the procedure, when the surgeon had to understand how strong to grasp the device to prevent slippage. This required about 20 min. After that, the surgeon was able to operate the device 304 without losing the grip. The wireless link was always reliable, resulting in an average RSSI of −33.4 dBm with losses between 4.8% and 6.2% of the total packages. Battery operation was effective for the entire procedure.

It is worth mentioning that the surgeon noted that a tether tied to the device would help in the retrieval at the end of the procedure. A wired connection may also provide power to the device instead of the battery, thus allowing for a reduction in size. On the other hand, a tether may limit device 304 motion and get trapped in between instruments.

Various features and advantages of the invention are set forth in the following claims.

What is claimed is:

1. A system for detecting a tissue property, the system including:
    a first unit positioned outside a patient body, the first unit including
        a first housing, and
        a first magnetic field source supported by the first housing; and
    a second unit positioned inside a patient body, the second unit including
        a second housing,
        a second magnetic field source supported by the second housing,
        a pressure sensor supported by the second housing,
        a localization module supported by the second housing, a controller, and a power source;

wherein the pressure sensor is configured to detect an indentation force applied to the tissue, wherein the indentation force is applied when the first magnetic field source and the second magnetic field source are magnetically coupled;

wherein the second unit is configured to wirelessly transmit the indentation force data and localization data to a computer to generate a volumetric stiffness map for the tissue.

2. The system of claim 1, wherein the localization module comprises a plurality of magnetic field sensors and an inertial sensor.

3. The system of claim 2, wherein the magnetic field sensors and the inertial sensor track a depth of the indentation applied to the tissue and a position of the second housing relative to the first magnetic field source.

4. The system of claim 2, wherein the magnetic field sensors comprise Hall effect sensors, and wherein at least three of the Hall effect sensors are mounted on three surfaces orthogonal to each other.

5. The system of claim 2, wherein the magnetic field sensor detects a magnetic field generated by the magnetic field source to determine a location and orientation of the second housing with respect to the magnetic field source.

6. The system of claim 1, wherein the localization data comprises data related to a position of the second unit when the indentation force is applied.

7. The system of claim 1, wherein the second housing comprises a cylindrical-shaped body having a first end and a second end, and wherein the pressure sensor is adjacent the first end.

8. The system of claim 7, wherein the second housing further comprises a grasping site for a tool to grip the second housing.

9. The system of claim 8, wherein the grasping site comprises a reduced diameter area on the second housing closer to the first end than the second end.

10. The system of claim 1 further comprising a computer system in communication with the controller, and wherein the computer system is configured to receive signals transmitted by the controller.

11. The system of claim 10, wherein the computer system further comprises a processor and a software program configured to process the signals from the controller to generate the volumetric stiffness map.

12. The system of claim 1, wherein the first unit further comprises an inertial sensor supported by the first housing.

13. A device insertable through an incision in a human body to determine tissue stiffness, the device comprising:

an enclosed housing having a first end and a second end;

a first magnetic field source supported within the enclosed housing;

a pressure sensor positioned at the first end of the housing;

a localization module supported within the enclosed housing;

a controller supported within the enclosed housing; and a power source supported within the enclosed housing and configured to provide power to the controller;

wherein the pressure sensor is configured to detect an indentation force applied to the tissue, wherein the indentation force is applied when the first magnetic field source is magnetically coupled to a second magnetic field source located external to the device;

wherein the localization module is configured to determine a position of the housing relative to the second magnetic field source when the indentation force is applied to the tissue; and wherein the controller is configured to wirelessly transmit the indentation force data and the localization data to a computer to generate a volumetric stiffness map for the tissue.

14. The device of claim 13, wherein the localization module comprises a plurality of magnetic field sensors and an inertial sensor for determining the position of the housing.

15. The device of claim 14, wherein the magnetic field sensors comprise Hall effect sensors, and wherein at least three of the Hall effect sensors are mounted on three surfaces orthogonal to each other that are supported within the enclosed housing.

16. The device of claim 15 further comprising a signal conditioning module positioned within the enclosed housing and configured to condition signals from the magnetic field sensors.

17. The device of claim 16 further comprising a power regulation module positioned within the enclosed housing and configured to monitor the power source and to provide an appropriate amount of power to the signal conditioning module.

18. The device of claim 13, wherein the pressure sensor comprises a barometric pressure sensor.

19. The device of claim 13 further comprising a transceiver configured to receive the indentation force data and the localization data from the controller and to transmit the indentation force data and the localization data to the computer.

20. A method for detecting a tissue property, the method including:

positioning a first unit outside of a patient body near a region of interest, the first unit including a first housing that supports a first magnetic field source;

positioning a second unit inside the patient body at the region of interest, the second unit including a second housing that supports a pressure sensor, a second magnetic field source, a plurality of magnetic field sensors, and an inertial sensor;

magnetically coupling the first magnetic field source and the second magnetic field source;

applying pressure on the region of interest with the second unit;

determining a tissue reaction pressure based on the pressure applied to the region of interest;

determining an indentation depth of the tissue when the pressure is applied to the region of interest, wherein the indentation depth is a function of a distance between the first magnetic field source and the second magnetic field source;

determining a position of the second unit when the pressure is applied to the region of interest;

wirelessly transmitting the tissue reaction pressure and the position data to a computer; and generating a tissue stiffness map based on the tissue reaction pressure, the tissue indentation depth, and the position of the second unit.

* * * * *